US012797434B2

(12) United States Patent
Sardeshmukh et al.

(10) Patent No.: US 12,797,434 B2

(45) **Date of Patent: *Nov. 17, 2026**

(54) PHARMACEUTICAL KIT FOR ALLEVIATING ADVERSE EFFECTS OF CHEMOTHERAPY

(71) Applicant: Sadanand Prabhakar Sardeshmukh, Pune (IN)

(72) Inventors: Sadanand Prabhakar Sardeshmukh, Pune (IN); Vineeta Vasant Deshmukh, Pune (IN)

(73) Assignee: Sadanand Sardeshmukh, Pune (IN)

(*) Notice: Subject to any disclaimer, the term of this patent is extended or adjusted under 35 U.S.C. 154(b) by 972 days.

This patent is subject to a terminal disclaimer.

(21) Appl. No.: 17/609,673

(22) PCT Filed: Feb. 12, 2020

(86) PCT No.: PCT/IB2020/051120

§ 371 (c)(1),
(2) Date: Nov. 8, 2021

(87) PCT Pub. No.: WO2020/225612

PCT Pub. Date: Nov. 12, 2020

(65) Prior Publication Data

US 2022/0226419 A1 Jul. 21, 2022

(30) Foreign Application Priority Data

May 7, 2019 (IN) ............................ 201921018276

(51) Int. Cl.

| | |
|---|---|
| ***A61K 36/899*** | (2006.01) |
| ***A61K 33/242*** | (2019.01) |
| ***A61K 35/20*** | (2006.01) |
| ***A61K 35/614*** | (2015.01) |
| ***A61K 35/618*** | (2015.01) |
| ***A61K 36/59*** | (2006.01) |
| ***A61K 36/736*** | (2006.01) |
| ***A61K 36/744*** | (2006.01) |
| ***A61K 36/81*** | (2006.01) |
| ***A61K 47/36*** | (2006.01) |

(52) U.S. Cl.

CPC .......... *A61K 36/899* (2013.01); *A61K 33/242* (2019.01); *A61K 35/20* (2013.01); *A61K 35/614* (2013.01); *A61K 35/618* (2013.01); *A61K 36/59* (2013.01); *A61K 36/736* (2013.01); *A61K 36/744* (2013.01); *A61K 36/81* (2013.01); *A61K 47/36* (2013.01)

(58) Field of Classification Search

None

See application file for complete search history.

(56) References Cited

U.S. PATENT DOCUMENTS

2018/0318374 A1 11/2018 Shetty

OTHER PUBLICATIONS

Deshmukh, V. et.al, Effectiveness of combinations of Ayurvedic drugs in alleviating drug toxicity and improving quality of life of cancer patients treated with chemotherapy. „ Supportive Care in Cancer, 2 014, 22(11), 3007-3015. doi:10.1007/s00520-014-2294-0.

Deshpande, A., "Assessment of Effect of CG4 (An Ayurvedic Formulation) in The Management of Side Effects of Chemotherapy in Breast Cancer", A thesis submitted to Tilak Maharashtra Vidvaoeeth, Pune for the Degree of Doctor of Philosophy (Ph. D.) Month & Year: Dec. 2016; URI: http://hdl.handle.net/10603/155158.

Gujar, S.R., "Role of RG4 an Ayurvedic formulation in the management of side effects of radiotherapy of oral cavity cancers", A thesis submitted to Tilak Maharashtra Vidyapeeth, Pune For the Degree of Doctor of Philosophy (Ph. D.), Month & Year : Sep. 2015; URL: http://hdl.handle.net/10603/87035.

PCT International Search Report for International Application No. PCT/IB2020/051120, completed Jul. 31, 2020, 3pp.

PCT Written Opinion for International Application No. PCT/IB2020/051120, completed Jul. 31, 2020, 6pp.

*Primary Examiner* — Susan Hoffman

(74) *Attorney, Agent, or Firm* — The Roy Gross Law Firm, LLC; Roy D. Gross

(57) ABSTRACT

The present disclosure relates to a pharmaceutical kit for alleviating adverse effects of chemotherapy, reducing oxidative stress, improving immunomodulatory response and quality of life. The pharmaceutical kit comprises Suvarna bhasmadi Vati (SBD), Mouktikyukta Kamdudha Vati (MKD), Padmakadi Ghrut (PDG), and Ananta vati. The pharmaceutical kit of the present disclosure can be used for alleviating adverse effects of chemotherapy such as nausea, vomiting, anorexia, fever, taste alteration, fatigue, dyspepsia, and mucositis. It can also improve immune status and reduce oxidative stress leading to betterment of the quality of life of the patients treated with chemotherapy. The pharmaceutical kit of the present disclosure may be beneficial in cancers and diseases for which chemotherapy is a treatment of choice.

12 Claims, 27 Drawing Sheets

PHARMACEUTICAL KIT FOR ALLEVIATING ADVERSE EFFECTS OF CHEMOTHERAPY

CROSS REFERENCE TO RELATED APPLICATIONS

This application is a National Phase of PCT Patent Application No. PCT/IB2020/051120, having International filing date of Feb. 12, 2020, which claims the benefit of priority of Indian Patent Application number 201921018276, filed May 7, 2019, the contents of which are all incorporated herein by reference in their entirety.

FIELD

The present disclosure relates to a pharmaceutical kit. Particularly, the present disclosure relates to a pharmaceutical kit for alleviating adverse effects of chemotherapy, and improving immunomodulatory response and quality of life.

Abbreviations

WBC: White blood cells.
SGOT: Serum glutamic oxaloacetic transaminase.
SGPT: Serum glutamic pyruvic transaminase.
RSR: Respective survival rate
QoL: Quality of Life
QLQ C 30: Quality of Life Questionnaire.

Definitions

As used in the present disclosure, the following terms are generally intended to have the meaning as set forth below, except to the extent that the context in which they are used indicate otherwise.

Suvarna bhasma: The term "Suvarna bhasma" refers to "incinerated gold" prepared by incinerating gold in accordance with the present disclosure. The term "Suvarna bhasma" referred in the present disclosure is not the same, as used in the Ayurveda. Suvarna refers to 24 carat gold.

Mouktik bhasma: The term "Mouktik bhasma" refers to "incinerated pearl", natural or cultured, prepared by incinerating pearl in accordance with the present disclosure. The term "Mouktik bhasma" referred in the present disclosure is not the same, as used in the Ayurveda.

Guduchi Sattva: The term "Guduchi Sattva" refers to extract comprising mainly starch of *Tinospora cordifolia/sinensis/crispa/glabra* prepared by alcoholic, hydro-alcoholic or aqueous extraction method. The term "Guduchi Sattva" referred in the present disclosure is not the same, as used in the Ayurveda.

Padmak: The term "Padmak" refers to "*Lotus/Nelumbo nucifera*".

Durva: The term Durva refers to "Burmuda grass/*Cynodon dactylon*".

Ananta: The term Ananta refers to "Swallow root (*Decalepis hamiltonii*) or *Hemidesmus indicus* or *Cryptolepis buchnani* or *Ichnocarpus frutescens.*"

Ghrut: The term "Ghrut" refers to "clarified butter" or "Cow's Ghee".

Shankha bhasma: The "Shankha bhasma" refers to "incinerated Conch shell". The term "Shankha bhasma" referred in the present disclosure is not the same, as used in the Ayurveda.

Shouktik bhasma: The term "Shouktik bhasma" refers to "incinerated empty pearl shell". The term "Shouktik bhasma" referred in the present disclosure is not the same, as used in the Ayurveda.

Kapardika bhasma: The "Kapardika Bhasma" refers to "incinerated Cowries". The term "Kapardika Bhasma" referred in the present disclosure is not the same, as used in the Ayurveda.

Pravala bhasma: The "Pravala Bhasma" refers to "incinerated coral". The term "Pravala Bhasma" referred in the present disclosure is not the same, as used in the Ayurveda.

Shudhha Gairik: The "Gairik" is a natural clay earth pigment which is a mixture of ferric oxide and varying amounts of clay and sand. "Shudhha Gairik" refers to "processed Gairik", prepared by roasting Gairik in ghee obtained from cow's milk. The term "Gairik" referred in the present disclosure is not the same, as used in the Ayurveda.

Vati: The term "Vati" refers to a method of medicine preparation in which herbs, minerals, and metallic compounds are compressed into tablet form.

Wick test: The term "wick test" refers to igniting a wick made out of residual solid part after separating Ghrut. Crackling sound of ignited wick indicates presence of water.

Trituration: The term "trituration" refers to either reducing the particle size of a substance or production of a homogeneous material by mixing component materials thoroughly or wet grinding any material with a liquid media like fresh juice or decoction etc.

Karnofsky score: The term "Karnofsky score" refers to the Karnofsky Performance Scale Index allows patients to be classified as to their functional impairment Symptom score: Symptom score of QLQ is indicative of symptomatology; hence decrease in symptom score represents both decrease in disease related symptoms and adverse effects of conventional treatment.

Function score: Functional score of QLQ signifies status of routine physical activities. Increase in functional scores represents improvement in QoL.

Global score: Global score of QLQ represents overall well-being of a patient. Increase in global scores represents improvement in QoL.

BACKGROUND

The background information herein below relates to the present disclosure but is not necessarily prior art.

By definition, chemotherapy includes the treatment of disease by means of chemicals that destroy cancerous tissue (anticancer therapy) or that have a specific toxic effect upon the disease producing microorganisms (antibiotics). This treatment modality produces favorable outcome in various cancers and bacterial diseases. However, it also produces generalized toxic effects such as nausea, vomiting, diarrhoea, fever, fatigue, skin discoloration, rigours, and the like, reduces immune response, increases oxidative stress, and hampers the quality of life, predominantly in cancers.

Breast cancer is a common malignancy in women worldwide. It ranks second to cervical cancer among cancers in females in India. The burden of breast cancer is increasing in both developed and developing countries. An increasing trend in incidence of breast cancer in India is reported from various registries of the National Cancer Registry Programme of the Indian Council of Medical Research.

The primary treatment for breast cancer is surgery. Surgery is often followed by chemotherapy. Chemotherapy is used to reduce the primary tumour load as well as recurrence and metastasis. Chemotherapy induces adverse side effects which are mainly caused by the inability of chemotherapeutic drugs to distinguish between dividing cancer cells and normal cells leading to increase in oxidative stress and hampered immune status. The other main adverse side effects include nausea, vomiting, loss of appetite, diarrhoea, constipation, weakness, alopecia (loss of hair), and early/late manifestations such as hepatotoxicity, renal toxicity and neurological problems. The early adverse side effects interfere with patient compliance and result in poor quality of life of patients. Further, the side effects such as myelo-suppression and liver and bladder toxicities may require discontinuation of therapy itself.

Efforts have been made to overcome these side effects by using alternative or adjunct therapies. However, these therapies used so far did not show effective reduction in the side effects.

Therefore, there is felt a need to provide a selected combination of herbo mineral and metallic compositions, in the form of a kit, that mitigates the aforestated problems.

OBJECTS

Some of the objects of the present disclosure, which at least one embodiment herein satisfies, are as follows:

An object of the present disclosure is to ameliorate one or more problems of the prior art or to at least provide a useful alternative.

Another object of the present disclosure is to provide a pharmaceutical kit.

Still another object of the present disclosure is to provide a pharmaceutical kit for alleviating adverse effects of chemotherapy.

Another object of the present disclosure is to provide a pharmaceutical kit for reducing oxidative stress in patients administered with chemotherapy.

Yet another object of the present disclosure is to provide a pharmaceutical kit for improving the immune response in patients administered with chemotherapy.

Still another object of the present disclosure is to provide a pharmaceutical kit for improving the quality of life in patients administered with chemotherapy.

Other objects and advantages of the present disclosure will be more apparent from the following description, which is not intended to limit the scope of the present disclosure.

SUMMARY

The present disclosure provides a pharmaceutical kit comprising a first container containing Suvarna Bhasmadi Vati (SBD) in a solid dosage form, a second container containing Mouktikyukta Kamdudha Vati (MKD) in a solid dosage form, a third container containing Padmakadi Ghrut (PDG) in a thick, viscous form, and a fourth container containing Ananta vati in a solid dosage form.

The SBD comprises Suvarna bhasma in an amount ranging from 2 wt % to 7 wt % of the total weight of the SBD, Mouktik bhasma in an amount ranging from 20 wt % to 35 wt % of the total weight of the SBD, Guduchi sattva in an amount ranging from 45 wt % to 60 wt % of the total weight of the SBD and at least one excipient in an amount ranging from 5 wt % to 30 wt % of the total weight of the SBD. In accordance with an embodiment of the present disclosure, the SBD comprises Suvarna bhasma in an amount ranging from 3 wt % to 5 wt % of the total weight of the SBD, Mouktik bhasma in an amount ranging from 23 wt % to 30 wt % of the total weight of the SBD, Guduchi sattva in an amount ranging from 48 wt % to 54 wt % of the total weight of the SBD, and at least one excipient in an amount ranging from 10 wt % to 25 wt % of the total weight of the SBD.

In an exemplary embodiment of the present disclosure, the SBD comprises Suvarna bhasma in an amount of 4.22 wt % of the total weight of the SBD, Mouktik bhasma in an amount of 26.37 wt % of the total weight of the SBD, Guduchi sattva in an amount of 52.74 wt % of the total weight of the SBD and gum acacia in an amount of 16.67 wt % of the total weight of the SBD.

The MKD comprises Mouktik bhasma in an amount ranging from 10 wt % to 14 wt % of the total weight of the MKD, Shankha bhasma in an amount ranging from 10 wt % to 14 wt % of the total weight of the MKD, Shouktik bhasma in an amount ranging from 10 wt % to 14 wt % of the total weight of the MKD, Kapardik bhasma in an amount ranging from 10 wt % to 14 wt % of the total weight of the MKD, Praval bhasma in an amount ranging from 10 wt % to 14 wt % of the total weight of the MKD, Guduchi sattva in an amount ranging from 10 wt % to 14 wt % of the total weight of the MKD, Shudhha Gairik in an amount ranging from 10 wt % to 14 wt % of the total weight of the MKD, and at least one excipient in an amount ranging from 10 wt % to 30 wt % of the total weight of the MKD. In an exemplary embodiment of the present disclosure, the MKD comprises equal quantities of Mouktik bhasma, Shankha bhasma, Shouktik bhasma, Kapardik bhasma, Praval bhasma, Guduchi sattva and Shudhha Gairik i.e. 12 wt % each, and at least one edible binder, typically a natural gum, in an amount of 16 wt % of the total weight of the MKD.

The PDG comprises extracts of Padmak, Durva and Ananta dissolved or dispersed in cow's ghee.

PDG comprises an extract of petals and stalks of *Nelumbo nucifera* in an amount ranging from 13 wt % to 20 wt % of the total weight of the composition; an extract of whole plant of *Cynodon dactylon* in an amount ranging from 13 wt % to 20 wt % of the total weight of the composition; a decoction of roots of *Decalepis hamiltonii* in an amount ranging from 13 wt % to 20 wt % of the total weight of the composition; and cow's ghee in an amount ranging from 40 wt % to 60 wt % of the total weight of the composition.

In an exemplary embodiment of the present disclosure, PDG contains extract of petals and stalks of *Nelumbo nucifera* is in an amount of 16.66 wt % of the total weight of the composition; the extract of whole plant of *Cynodon dactylon* is in an amount of 16.66 wt % of the total weight of the composition; the decoction of roots of *Decalepis hamiltonii* is in an amount of 16.66 wt % of the total weight of the composition; and the clarified butter is in an amount of 50 wt % of the total weight of the composition.

The Ananta Vati comprises powder obtained from dried roots of Ananta in an amount ranging from 75 wt % to 92 wt % of the total weight of the Ananta Vati, wherein the powder has a particle size in the range of 150 to 180 microns, and at least one excipient in an amount ranging from 8 wt % to 25 wt % of the total weight of the Ananta Vati. The Ananta is *Decalepis hamiltonni.*

The compositions of SBD, MKD, and Ananta Vati are prepared in the form of solid unit dosage form selected from the group consisting of tablet, pill, and capsule.

BRIEF DESCRIPTION OF THE ACCOMPANYING DRAWING

The present disclosure will now be described with the help of the accompanying drawing, in which:

FIG. 1A and FIG. 1B depict the results of clinical investigation for anorexia, wherein Study group is denoted by 'X' and Control group is denoted by 'Y'. Low degree adverse effect is denoted by 'P' and High degree adverse effect is denoted by 'Q' in FIG. 1B;

Figure 42A:
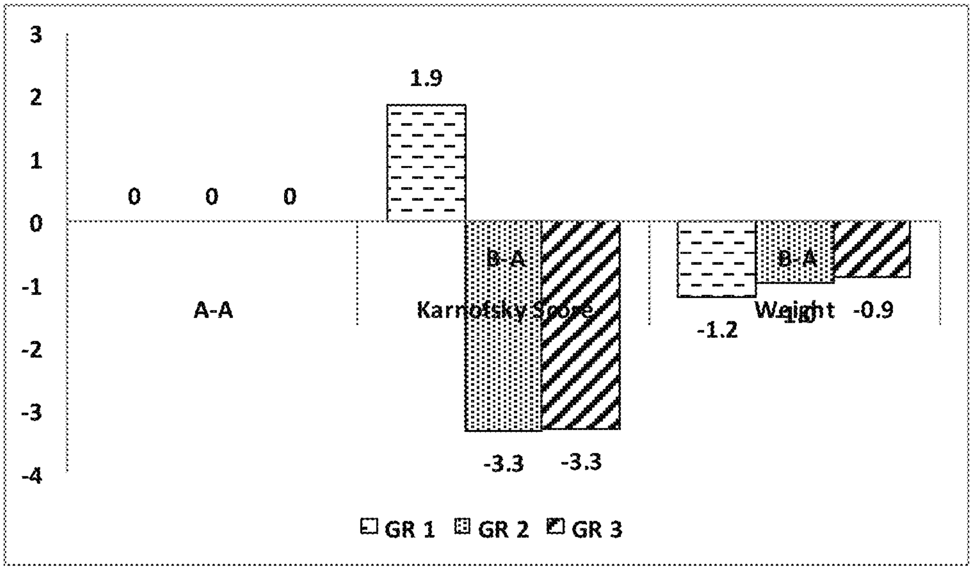
Figure 42B:
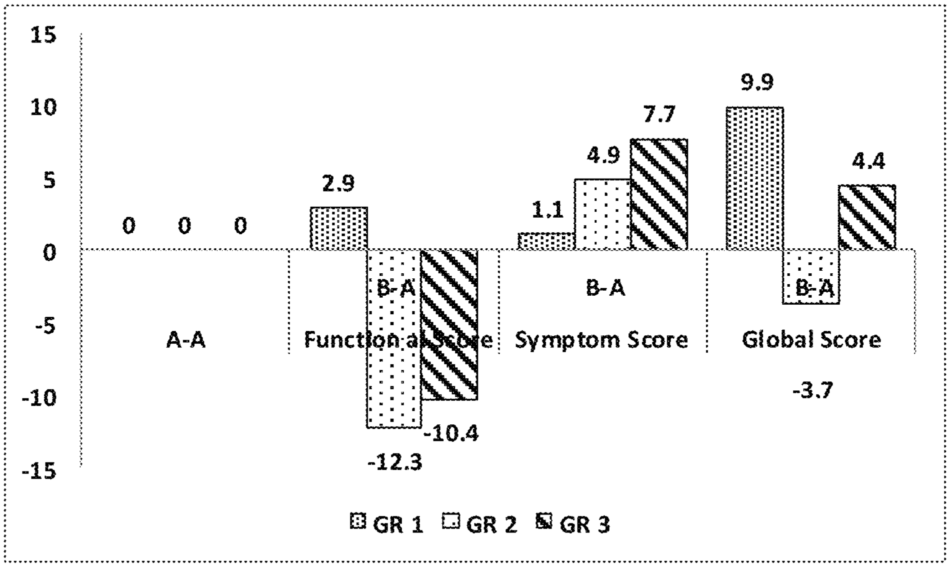

FIG. 42A depicts a graphical representation showing comparison of quality of life (Karnofsky score, weight,) in group treated with present pharmaceutical kit (GR1), treated with combination of MKD, Ananta vati, Praval Pishti and PDG (GR2) and control group (GR3); and FIG. 42B depicts a graphical representation showing comparison of quality of life (functional score, symptom score and global score) in group treated with present pharmaceutical kit (GR1), treated with combination of MKD, Ananta vati, Praval Pishti and PDG (GR2) and control group (GR3).

DETAILED DESCRIPTION

Embodiments, of the present disclosure, will now be described with reference to the accompanying drawing.

Embodiments are provided so as to thoroughly and fully convey the scope of the present disclosure to the person skilled in the art. Numerous details are set forth, relating to specific components, and methods, to provide a complete understanding of embodiments of the present disclosure. It will be apparent to the person skilled in the art that the details provided in the embodiments should not be construed to limit the scope of the present disclosure. In some embodiments, well-known processes, well-known apparatus structures, and well-known techniques are not described in detail.

The terminology used, in the present disclosure, is only for the purpose of explaining a particular embodiment and such terminology shall not be considered to limit the scope of the present disclosure. As used in the present disclosure, the forms "a," "an," and "the" may be intended to include the plural forms as well, unless the context clearly suggests otherwise. The terms "comprises," "comprising," "including," and "having," are open ended transitional phrases and therefore specify the presence of stated features, integers, steps, operations, elements, modules, units and/or components, but do not forbid the presence or addition of one or more other features, integers, steps, operations, elements, components, and/or groups thereof. The particular order of steps disclosed in the method and process of the present disclosure is not to be construed as necessarily requiring their performance as described or illustrated. It is also to be understood that additional or alternative steps may be employed.

The incidence of breast cancer is increasing in women worldwide. Chemotherapy is used to reduce the primary tumour load as well as recurrence and metastasis. Although, chemotherapy is an unavoidable line of treatment for cancer, the adverse effects of chemotherapy frequently interfere with continuation of chemotherapy. The adverse effects are due to generation of oxidative stress, inability to control inflammation, reduction in immune response and functional impairment in tissues. These destructive effects result in impairment of quality of life of patients.

Therefore, the present disclosure provides a selected combination of pharmaceutical compositions, in the form of a kit.

The present disclosure deals with alleviating adverse side effects of chemotherapy, controlling oxidative stress, improving immune response and quality of life, if administered along with and continued after chemotherapy treatment.

In an aspect of the present disclosure, there is provided a pharmaceutical kit for alleviating immediate, intermediate, and late adverse effects of chemotherapy, reducing oxidative stress, improving immune status and quality of life.

The pharmaceutical kit comprising a first container containing Suvarna Bhasmadi Vati (SBD) in a solid dosage form, a second container containing Mouktikyukta Kamdudha Vati (MKD) in a solid dosage form, a third container containing Padmakadi Ghrut (PDG) in a thick, viscous form, and a fourth container containing Ananta vati in a solid dosage form.

A combination of SBD, MKD, PDG, and Ananta Vati in the kit is used for minimizing the adverse effects of chemotherapy and improving the quality of life. The adverse effects of chemotherapy are observed due to hampered function of gastrointestinal (GI) system, generation of oxidative stress, inability to control inflammation, reduction in immune response and functional impairment in tissues. These malfunctions are effectively corrected by the selected combination of pharmaceutical compositions, in the form of a kit, of the present disclosure.

The rationale for selecting the individual components of the kit and their compositions are as follows:

Suvarna Bhasmadi Vati (SBD) prepared in accordance with the present disclosure has been found to have the following effects in managing the adverse side effects of chemotherapy. SBD provides nourishment to body as well as to tissues which are hampered due to conventional systemic anti-cancer therapies. The anti-cancer therapies interfere with normal functions of GI system, produce inflammation in GI system, and interfere with the process of absorption of micro nutrients at cellular level. These malfunctions are effectively corrected by SBD. The quantities of Suvarna bhasma, Mouktik bhasma, and Guduchi sattva are carefully triturated. Although potency and duration of effectiveness of Suvarna bhasma is satisfactory, the addition of Mouktik bhasma and Guduchi sattva is needed for its easy absorption. Combining Suvarna bhasma with Mouktik bhasma and Guduchi sattva pacifies the aggressiveness of Suvarna Bhasma capacity on the digestive power as well as absorption at tissue level of the patient. Additionally Mouktik Bhasma has an antacid effect whereas Guduchi sattva is anti-pyretic and immunomodulator.

PDG in its unique combination, assists in minimizing the side effects of chemotherapy by rectifying the disorders of gastro-intestinal system, detoxifying blood, reducing inflammation and imparting hepato-protection. Cow's ghee in PDG holds the components of PDG together and improved their mode of action synergistically.

Ananta vati has mainly detoxifying effect in the blood. The active components of Ananta in Ananta Vati have an immediate effect in detoxifying the blood whereas the active components of Ananta bound in PDG provide sustained response. These active components are probably released slowly thus had long lasting immunomodulatory effect and improvement in anti-oxidant activity.

Thus, when the kit is administered in the form of combination, the SBD helps in improving immunomodulatory activity and rejuvenation effect. MKD has anti-emetic and carminative activity. Ananta Vati provides immediate detoxification of the blood and acts as a free oxidative radical scavenging agent while PDG smoothens GI tract and improves gross as well as micro level absorption, thus improving metabolism. All these four constituents of the pharmaceutical kit of present disclosure act synergistically in controlling ROS (Reactive oxygen species) generation, improving anti-inflammatory activity and immunomodulation, therefore reducing adverse side effects of chemotherapy and improving quality of life in cancer patients.

By way of example, the present kit envisaged in this disclosure is suitable as an adjuvant in the treatment for breast cancer in alleviating adverse side effects of chemotherapy and improving quality of life of the patients.

The SBD in the present pharmaceutical composition comprises Suvarna bhasma in an amount ranging from 2 wt % to 7 wt % of the total weight of the SBD, Mouktik bhasma in an amount ranging from 20 wt % to 35 wt % of the total weight of the SBD, Guduchi sattva in an amount ranging from 45 wt % to 60 wt % of the total weight of the SBD, and at least one excipient in an amount ranging from 5 wt % to 30 wt % of the total weight of the SBD.

Suvarna bhasma is known as incinerated gold and Mouktik bhasma is known incinerated pearl. The amount below 2 wt %, the Suvarna Bhasma will be sub-therapeutic and in quantities greater than 7 wt %, there will be an overload of the Bhasma which will be excreted. Similarly, the lower and upper weight percentages of the other ingredients i.e. Mouktik Bhasma and Guduchi Sattva have been triturated in this formulation keeping the above principle in mind. Ideally, after experimentation it is found that for optimum effect of SBD the composition should contain 4 wt % Suvarna Bhasma, 26 wt % Mouktik Bhasma, and 53 wt % Guduchi Sattva which are bound together with a natural gum such as gum acacia to the extent of 17 wt %.

The ingredients in powder form are blended together. The natural gum is added to the powder blend to form a dough along with purified water. Pellets are formed from this dough having average weight of 5 gm. The pellets are tray-dried typically at temperature in the range of 40° C. to 45° C. The dried pellets are granulated in a mixer grinder and the dry granules are taken for compression tableting. The average weight of the uncoated tablets is 240 mg±5%. The typical shelf life of the tablets is 3 years.

Guduchi is the common name for *Tinospora*. The *Tinospora* (Guduchi) plant is selected from *Tinospora cordifolia* and *Tinospora sinensis*. Particularly the stem of the plant is used for making the Sattva.

*Tinospora cordifolia* is also known as Guduchi of the family Menispermaceae. *Tinospora cordifolia* is indigenous to the tropical areas of India, Myanmar, and Sri Lanka. *Tinospora cordifolia* is obtained from Bharatiya Sanskriti Darshan Trust (BSDT), Wagholi, Pune.

*Tinospora sinensis* is also known as Malabar Gulbel or Gulvel of the family Menispermaceae. *Tinospora sinensis* is found in India, China, Sri Lanka, Nepal, Cambodia, Thailand, Vietnam, and Myanmar *Tinospora sinensis* is obtained from Bharatiya Sanskriti Darshan Trust (BSDT), Wagholi, Pune.

In an embodiment of the present disclosure, the excipient is binder. The binder is selected from the group consisting of gum acacia, guar gum, and xanthan gum.

The SBD is administered at a dose of 800 mg to 1000 mg per day by oral administration.

The MKD in the present pharmaceutical composition comprises Mouktik bhasma in an amount ranging from 10 wt % to 14 wt % of the total weight of the MKD, Shankha bhasma in an amount ranging from 10 wt % to 14 wt % of the total weight of the MKD, Shouktik bhasma in an amount ranging from 10 wt % to 14 wt % of the total weight of the MKD, Kapardik bhasma in an amount ranging from 10 wt % to 14 wt % of the total weight of the MKD, Praval bhasma in an amount ranging from 10 wt % to 14 wt % of the total weight of the MKD, Guduchi sattva in an amount ranging from 10 wt % to 14 wt % of the total weight of the MKD, Shudhha Gairik in an amount ranging from 10 wt % to 14 wt % of the total weight of the MKD, and at least one excipient in an amount ranging from 10 wt % to 30 wt % of the total weight of the MKD.

The quantities below 10 wt % the Mouktik Bhasma will be sub-therapeutic and in quantities greater than 14 wt %, there will be an overload of the Bhasma which will be excreted.

Similarly, the lower and upper weight percentages of the other ingredients i.e. Praval Bhasma, Shankha Bhasma, Shouktik Bhasma, Kapardik Bhasma, Shudhha Gairik, and Guduchi Sattva have been triturated in this formulation keeping the above principle in mind. Ideally, after experimentation, it is found that for optimum effect of MKD the composition should contain equal amounts (12 wt % each) of Mouktik Bhasma, Praval Bhasma, Shankha Bhasma, Shouktik Bhasma, Kapardik Bhasma, Shudhha Gairik, and Guduchi Sattva as stated in classical texts, which are bound together with a natural gum such as gum acacia to the extent of 16 wt %. The ingredients in powder form are blended together. The natural gum is added to the powder blend to form a dough using purified water. Pellets are formed from this dough having average weight of 5 gm each. The pellets are tray-dried typically at temperature in the range of 40° C. to 45° C. The dried pellets are granulated in a mixer grinder and the dry granules are taken for compression tableting. The average weight of each uncoated tablet is 300 mg±5%. The typical shelf life of the tablets is 3 years.

The *Tinospora* (Guduchi) plant is selected from *Tinospora cordifolia* and *Tinospora sinensis*.

*Tinospora cordifolia* is also known as Guduchi of the family Menispermaceae. *Tinospora cordifolia* is indigenous to the tropical areas of India, Myanmar, and Sri Lanka. It is obtained from Bharatiya Sanskriti Darshan Trust, Pune.

*Tinospora sinensis* is also known as Malabar Gulbel or Gulvel of the family Menispermaceae. *Tinospora sinensis* is found in India, China, Sri Lanka, Nepal, Cambodia, Thailand, Vietnam, and Myanmar. It is obtained from Bharatiya Sanskriti Darshan Trust, Pune.

In one embodiment, the MKD comprises equal quantities of Mouktik bhasma, Shankha bhasma, Shouktik bhasma, Kapardik bhasma, Praval bhasma, Guduchi sattva and Shudhha Gairik and at least one edible binder, typically a natural gum, in an amount ranging from 10 wt % to 30 wt % of the total weight of the MKD.

In an embodiment of the present disclosure, the excipient is a binder, selected from the group consisting of gum acacia, guar gum, and xanthan gum.

The MKD is administered at a dose of 800 mg to 1200 mg per day by oral administration.

The PDG comprises:

i) extract of petals and stalks of Padmak, wherein the extract of Padmak is an extract obtained using at least one solvent selected from the group consisting of alcohol, water and a mixture thereof. Alternatively the extract is obtained by supercritical extraction;

ii) extract of whole Durva plant, wherein the extract of Durva is obtained using at least one solvent selected from the group consisting of alcohol, water and a mixture thereof. Alternatively the extract is obtained by supercritical extraction;

iii) decoction of roots of Ananta, wherein the decoction of Ananta is obtained using at least one solvent selected from the group consisting of alcohol, water, and a mixture thereof. Alternatively the extract is obtained by supercritical extraction; and iv) Ghee obtained from cow's milk in an amount ranging from 90 wt % to 98 wt % of the total weight of the PDG.

The amount of the combined extract of petals and stalks of Padmak, whole Durva plant, and roots of Ananta is in the range of 2 wt % to 10 wt % of the total weight of PDG, and wherein the weight ratio of the extract of petals and stalks of Padmak to the extract of whole Durva plant to the decoction of roots of Ananta is 1:1:1.

Fresh juice of flower petals and stalks of Padmak, fresh juice of whole plant of Durva, and aqueous decoction of roots of Ananta are mixed with cow's ghee. The mixture is heated uniformly with stirring to evaporate the water completely. The complete removal of water is confirmed by the wick test. The active ingredients of the juices and decoction are dissolved or dispersed in the hot ghee. The hot mixture so obtained was filtered through muslin cloth to obtain PDG. The expiry of PDG is 2 years.

*Nelumbo nucifera* is commonly known as Padmak. *Nelumbo nucifera* is of the family Nymphaceae and the genus *Nelumbo. Nelumbo nucifera* is found in India, Sri Lanka, virtually all of Southeast Asia, New Guinea and northern and eastern Australia. *Nelumbo nucifera* is obtained from Bharatiya Sanskriti Darshan Trust, Wagholi, Pune.

*Cynodon dactylon* is commonly known as Durva of the family Poaceae. *Cynodon dactylon* is originated in the Middle East. It is also found in India, Bermuda, and North America. *Cynodon dactylon* is obtained from Bharatiya Sanskriti Darshan Trust (BSDT), Wagholi, Pune.

Ananta is *Decalepis hamiltonni. Decalepis hamiltonii* is commonly used as Ananta. *Decalepis hamiltonii* is of the family Apocynaceae. It is found in South India. *Decalepis hamiltonii* is obtained from Bharatiya Sanskriti Darshan Trust (BSDT), Wagholi, Pune. Ananta is roots of *Decalepis hamiltonii* (Swallow roots) or *Hemidesmus indicus* or *Cryptolepis buchnani* or *Ichnocarpus frutescens*. In an embodiment, Ananta is *Decalepis hamiltonii* (Swallow roots). *Decalepis hamiltonii* (Swallow roots) is used due to commercial availability, however, it is asserted that *Hemidesmus indicus* or *Cryptolepis buchnani* or *Ichnocarpus frutescens* will equally be effective, alone or in combination with each other.

Cow Ghee is obtained from Bharatiya Sanskriti Darshan Trust (BSDT), Wagholi, Pune. PDG is administered at a dose of 8 gm to 12 gm per day by oral administration.

In an embodiment of the present disclosure, the PDG is prepared in the form of a thick viscous liquid.

The Ananta vati comprises powder obtained from dried roots of Ananta (*Decalepis hamiltonii*) in an amount ranging from 75 wt % to 92 wt % of the total weight of the Ananta vati, wherein the powder has a particle size in the range of 150 to 180 microns, and at least one excipient in an amount ranging from 8 wt % to 25 wt % of the total weight of the Ananta vati.

Ananta powder is mixed with natural gum to form a dough along with purified water. Pellets are formed from this dough having average of 5 gm. These pellets are tray dried typically at temperature in the range of 40-45° C. The dried pellets are granulated in a mixer grinder and the dry granules are taken for compression tableting. The average weight of the uncoated tablets is 300 mg±5%. The typical shelf life of these tablets is 3 years.

Ananta is *Decalepis hamiltonni. Decalepis hamiltonni* is obtained from Bharatiya Sanskriti Darshan Trust (BSDT), Wagholi, Pune. Other Ananta species such as *Hemidesmus indicus, Cryptolepis buchnani, Ichnocarpus frutescens*, and the like also can be used in the pharmaceutical kit of the present disclosure.

In an embodiment of the present disclosure, the excipient is gum acacia.

The Ananta vati is administered at a dose of 1.8 mg to 2.2 gm per day by oral route.

The compositions of SBD, MKD, and Ananta vati are prepared in the form of a solid unit dosage form selected from the group consisting of tablet, pill, and capsule.

The foregoing description of the embodiments has been provided for purposes of illustration and not intended to limit the scope of the present disclosure. Individual components of a particular embodiment are generally not limited to that particular embodiment, but, are interchangeable. Such variations are not to be regarded as a departure from the present disclosure, and all such modifications are considered to be within the scope of the present disclosure.

The present disclosure is further described in light of the following experiments which are set forth for illustration purpose only and not to be construed for limiting the scope of the disclosure. The following experiments can be scaled up to industrial/commercial scale and the results obtained can be extrapolated to industrial scale.

EXPERIMENTAL DETAIL

Example 1

A pharmaceutical kit was prepared in accordance with the present disclosure.

The components of the pharmaceutical kit containing oral medicines are given in Table-1.

TABLE 1

Components of the pharmaceutical kit containing oral medicines

| Sr. No. | Medicine | Quantity per dose | Time |
|---|---|---|---|
| 1 | SBD | 395 mg (2 tablets) | Morning after breakfast (8.00am)- Evening after snacks (5.00pm) |
| 2 | MKD | 500 mg (2 tablets) | Morning after breakfast (8.00am)- Evening after snacks (5.00pm) |

TABLE 1-continued

Components of the pharmaceutical kit containing oral medicines

| Sr. No. | Medicine | Quantity per dose | Time |
|---|---|---|---|
| 3 | PDG | 5 gm (1 tsp) | Before Lunch and Dinner |
| 4 | Ananta Vati | 1 gm (4 tablets) | After Lunch and Dinner |

Experiment 1: Composition of SBD in Accordance with the Present Disclosure

Result:

SBD was prepared using the following ingredients as given in Table-2.

TABLE 2

Composition of SBD

| Sr. No. | Contents | Latin name/ English Name | Quantity for 5 kg batch-Batch 1 | Quantity for 5 kg batch-Batch 2 | Quantity for 5 kg batch-Batch 3 |
|---|---|---|---|---|---|
| 1 | Suvarna Bhasma | Incinerated Gold | 210.97 g | 110 g | 350 g |
| 2 | Mouktik Bhasma | Incinerated Pearl | 1318.56 g | 1700 g | 1000 g |
| 3 | Aqueous extract of *Tinospora cordifolia/sinensis* | Starch of *Tinospora cordifolia/sinensis* | 2637.1 g | 2940 g | 2250 g |
| 4 | Gum Acacia powder | | 833.33 g | 250 g | 1400 g |

Process for Preparing SBD:

Step 1: Preparation of Suvarna Bhasma

Initially, 300 gm of Suvarna foils were amalgamated with 2500 gm of metallic mercury and 2500 gm of sulphur powder having particle size 150 microns and then incinerated 18 times each at 650° C. for 6 hours to get incinerated Suvarna. For stabilization, the incinerated Suvarna was triturated for 6 hours with 200 ml fresh juice of the leaves of *Ocimum sanctum* (Tulsi) and further incinerated at 600° C. for 5 hours. This process of incineration in Tulsi juice was repeated 25 times to obtain Suvarna Bhasma having particle size in the range of 20-500 nm (average particle size 350 nm). The particle size of the so obtained Suvarna Bhasma were analysed by particle size analyser (90 plus from Brookhaven Instruments, USA).

Tulsi—*Ocimum sanctum* is also known as holy basil of the family Lamiaceae. *Ocimum sanctum* was obtained from Bharatiya Sanskriti Darshan Trust (BSDT), Wagholi, Pune.

Specification of Suvarna Bhasma:

- Description: Brown coloured, very fine free flowing powder
- Loss on Drying—NMT 0.5% w/w
- Loss on Ignition—NMT 1% w/w
- Acid insoluble ash—90 to 98% w/w
- Assay as Au—NLT 85% w/w Step 2: Preparation of Mountie Bhasma 8 Kg Mountie (pearl) was boiled in 32 L of butter milk having curd to water ratio of 1:2 w/v and pH of 3, to obtain purified Mouktik. The so obtained purified Mouktik was powdered and triturated with 4 L of rose water to obtain triturated powder. The triturated powder was then incinerated using cow-dung cakes at 700° C. to obtain Mouktik Bhasma (incinerated pearl).

Specification of Mouktik Bhasma:

- Description: Greyish white coloured, very fine powder
- Loss on Drying—NMT 0.5% w/w
- Acid insoluble ash—NMT 2% w/w
- Calcium assay—38 to 40% w/w
- pH—10 to 11

Step 3: Extraction of Starch from *Tinospora cordifolia*

50 Kg of fresh stems of *Tinospora cordifolia* were chopped into small pieces. These pieces were crushed and then soaked for 12 hours in 4 times (w/v) of potable water (200 L) in a stainless steel vessel. The mixture was macerated in water thoroughly and filtered slowly to obtain solution containing aqueous extract of *Tinospora cordifolia*. The solution thus obtained was kept aside for 12 hours to obtain supernatant and smooth starchy sediment of *Tinospora cordifolia*. The supernatant was carefully separated to obtain smooth starchy sediment. The smooth starchy sediment of *Tinospora cordifolia* was evaporated in an oven at 45° C. to obtain Guduchi Sattva in the form of dry starch.

Specification of Starch Extract of *Tinospora cordifolia:*

- Description: Greyish white coloured very fine free flowing starchy powder
- Loss on Drying—NMT 5% w/w
- Acid insoluble ash—NMT 1% w/w
- Gelation temperature—60 to 75° C.

Step 4: Preparation of SBD

In a mixer, Suvarna bhasma, Mauktik bhasma, Guduchi Sattva (starch from *Tinospora cordifolia*), and gum acacia were mixed in a proportion given in Table 2. To this mixture, sufficient amount of water was added to obtain a dough. The dough was further pelletized to obtain pellets. The pellets were dried in oven at 45° C. to obtain dried pellets. The dried pellets were grinded to obtain granules having powder to granule ratio of 30:70. The mixture of granules and powder was compressed in tablet punching machine to obtain compressed tablet of weight 237±5 mg.

Specifications of SBD:

- Appearance: Grey colour, round
- Shape: Biconvex tablets
- Weight variation: 0.2210 to 0.2300
- Average weight: 0.2300 to 0.2500
- Hardness: 1-2 Kg/cm$^2$
- Friability: NMT 1% w/w
- Disintegration Time: NMT 30 min
- Diameter: 7 to 7.5 mm
- Width: 3.3 to 4.6 mm
- Acute toxicity: LD 50>2000 mg/kg Experiment 2: Composition of MKD in Accordance with the Present Disclosure
Result:

MKD was prepared using the following ingredients as given in Table-3.

TABLE 3

| Composition of MKD | | | | | |
|---|---|---|---|---|---|
| Sr. No. | Contents | Latin name/ English Name | Quantity for 30 kg batch- Batch 1 | Quantity for 30 kg batch- Batch 2 | Quantity for 30 kg batch- Batch 3 |
| 1 | Mouktik Bhasma | Incinerated Pearl | 3572 g | 3500 | 4000 |
| 2 | Shankha Bhasma | Incinerated Conch | 3572 g | 3000 | 3800 |
| 3 | Shouktik Bhasma | Incinerated Pearl Shell | 3572 g | 3000 | 3800 |
| 4 | Kapardik Bhasma | Incinerated Cowrie | 3572 g | 3000 | 3800 |
| 5 | Praval Bhasma | Incinerated Coral | 3572 g | 3500 | 3800 |
| 6 | An aqueous extract of *Tinospora cordifolia/sinensis* | Starch of *Tinospora cordifolia/sinensis* | 3572 g | 3500 | 4000 |
| 7 | Shudhha Gairik | Red ochre roasted in cow ghee | 3572 g | 3000 | 3800 |
| 8 | Gum Acacia powder | | 5000 g | 7500 | 3000 |

Process for Preparing MKD:

Mouktik bhasma, Shankha bhasma, Shouktik bhasma, Kapardik bhasma, Praval bhasma (all these five bhasma are prepared using textual methods), starch of *Tinospora cordifolia/sinensis*, Shudhha Gairik and gum acacia powder were mixed in a proportion given in Table 3. To this mixture, sufficient amount of potable water was added to obtain a dough. The dough was further pelletized to obtain pellets. The pellets were dried in oven at 45° C. to obtain dried pellets. The dried pellets were grinded to obtain granules having powder to granule ratio of 30:70. The mixture of granules and powder was compressed in tablet punching machine to obtain compressed tablet of weight 300±5 mg.

Specification of Shankha Bhasma:
- Description—Greyish white very fine powder
- Loss on drying—NMT 1% w/w
- Acid insoluble ash—NMT 2% w/w
- pH—9 to 10
- Calcium assay as Ca—38 to 40% w/w Specification of Shouktik Bhasma:
- Description—Greyish white very fine powder
- Loss on drying—NMT 1% w/w
- Acid insoluble ash—NMT 2% w/w
- pH—10 to 11
- Calcium assay as Ca—38 to 40% w/w Specification of Kapardik Bhasma:
- Description—Greyish white very fine powder
- Loss on drying—NMT 1% w/w
- Acid insoluble ash—NMT 2% w/w
- pH—10 to 11
- Calcium assay as Ca—38 to 40% w/w Specification of Praval Bhasma:
- Description—Greyish white very fine powder
- Loss on drying—NMT 1% w/w
- Acid insoluble ash—NMT 2% w/w
- pH—10 to 11
- Calcium assay as Ca—40 to 45 w/w Specification of Mouktik (Pearl) Bhasma:
- Description—Greyish white very fine powder
- Loss on drying—NMT 1% w/w
- Acid insoluble ash—NMT 2% w/w
- pH—10 to 11
- Calcium assay as Ca—38 to 40% w/w Specification of Shudhha Gairik (Red Ochre):
- Loss on drying—NMT 1% w/w
- Iron assay—NLT 15% w/w
- Silica assay—18 to 20% w/w
- Oil content—3 to 3.5% w/w Specification of Guduchi Sattva (Starch of *Tinospora cordifolia/Sinensis*):
- Loss on drying—4 to 5% w/w
- Acid Insoluble ash—NMT 1% w/w
- Gelation temperature—60 to 75° C.

Specification of MKD:
- Description: Light brown colour
- Shape: Round biconvex tablet
- Weight variation: 0.2850 to 0.3150
- Average weight: 0.2900 to 0.3100
- Hardness: 2 to 4 Kg/cm$^2$
- Friability: NMT 1% w/w
- Disintegration Time: NMT 30 min
- Diameter: 7 to 8 mm
- Width: 3 to 4 mm
- Acute Toxicity: LD 50>2000 mg/kg Experiment 3: Composition of PDG in Accordance with the Present Disclosure
Result:

PDG was prepared using the following ingredients as given in Table-4.

TABLE 4

| Sr. No. | Contents | Common Name | Quantity for 1 kg batch of finished product-Batch 1 | Quantity for 1 kg batch of finished product-Batch 2 | Quantity for 1 kg batch of finished product-Batch 3 |
|---|---|---|---|---|---|
| | Ingredients for preparing PDG | | | | |
| 1 | Aqueous extract of *Nelumbo nucifera* | Padmak | 333.33 ml | 250 ml | 400 ml |
| 2 | Aqueous extract of *Cynodon dactylon* | Durva | 333.33 ml | 250 ml | 400 ml |
| 3 | Decoction of *Decalepis hamiltonii* | Ananta | 333.34 ml | 250 ml | 400 ml |
| 4 | Clarified butter | Ghrut, Ghrita, Cow's ghee | 1000 g | 1000 g | 1000 g |

Process for Preparing PDG:

Step I: Preparation of Extract of Petals and Stalks of Flower of Padmak (*Nelumbo nucifera*)

300 gm of petals and stalks of flower of *Nelumbo nucifera* was obtained. The petals and stalks of flower of *Nelumbo nucifera* were chopped in pieces and soaked in water, for 12 hours wherein the petal to stalk ratio was 3:1 and the petals and stalks of *Nelumbo nucifera* to water ratio was 1:1.25. After 12 hours, the chopped pieces of petal and stalks of flowers of *Nelumbo nucifera* were separated from the water filtration to obtain an aqueous extract of petals and stalks of flower of *Nelumbo nucifera*, which was used in the preparation of the herbal composition.

Step II: Preparation of Extract of Whole Durva Plant (*Cynodon dactylon*)

Separately, 330 gm of whole plant of *Cynodon dactylon* was obtained, chopped into pieces and macerated in 660 ml of water to obtain macerated Durva plant. The macerated Durva plant was blended in water to obtain a blend, wherein the ratio of *Cynodon dactylon* to water was 1:2. The blend was filtered to obtain a filtrate contain extract of Durva which was used in the preparation of the herbal composition.

Step III: Preparation of Decoction of Ananta (*Decalepis hamiltonii*)

Further, 330 gm of dried roots of *Decalepis hamiltonii* was obtained and chopped into pieces. The chopped roots of *Decalepis hamiltonii* were separately undergoes decoction, wherein the ratio of *Decalepis hamiltonii* root to water was 1:8 and reduced to $\frac{1}{4}^{th}$ to obtain the decoction of *Decalepis hamiltonii*, which was used in the preparation of herbal composition The aqueous extract of flower petals and stalks of *Nelumbo nucifera* (obtained in the step I), aqueous extract of whole plant of *Cynodon dactylon* (obtained in step II), decoction of roots of *Decalepis hamiltonii* (obtained in step III), and clarified butter were mixed in a proportion given in Table 1. The so obtained mixture was heated uniformly at 100° C. for 60 minutes to evaporate water completely to obtain 1 kg of the herbal composition of the present disclosure.

Specification of Herbal Composition

Description: Greenish semi-solid granular (mass) paste
Specific gravity at 25° C.: 0.9040 to 0.9140
Refractive index at 25° C.: 1.535 to 1.545
Acid value: 1.3500 to 1.7500
Saponification value: 300 to 370
Unsaponifiable matter: 0.5 to 4
Iodine value: 25 to 45
Peroxide value: 0.5 to 1.5
Congealing point: 27 to 31
RM (Reichert-Meissl) value: 5 to 50
Moisture content: 0 to 0.5%

Experiment 4: Composition of Ananta Vati in Accordance with the Present Disclosure Result:

Ananta Vati was prepared using the following ingredients as given in Table-5.

TABLE 5

| Sr. No. | Contents | Common Name | Quantity for 30 kg batch-Batch 1 | Quantity for 30 kg batch-Batch 2 | Quantity for 30 kg batch-Batch 3 |
|---|---|---|---|---|---|
| | Composition of Ananta Vati | | | | |
| 1 | Powder of *Decalepis hamiltonii* | Ananta | 25000 g | 22500 | 27500 |
| 2 | Gum Acacia powder | | 5000 g | 7500 | 2500 |

Process for preparing Ananta Vati:

In a mass mixer, powders of *Decalepis hamiltonii* and gum acacia were mixed in a proportion given in Table 5. To this mixture, sufficient amount of potable water was added to obtain a dough. The dough was further pelletized to obtain pellets. The pellets were dried in oven at 45° C. to obtain dried pellets. The dried pellets were grinded to obtain granules having powder to granule ratio of 30:70. The granules and powder were compressed in tablet punching machine to obtain compressed tablet of weight 300±5 mg.

Specification of Ananta Vati:

Description: Light brown colour
Shape: Round biconvex tablets
Weight variation: 0.2850 to 0.3150
Average weight: 0.2900 to 0.3100
Hardness: 1 to 4 Kg/cm$^2$
Friability: NMT 1% w/w
Disintegration Time: NMT 15 min
Diameter: 10 to 11 mm
Width: 4 to 5 mm Example 2

Efficacy Study of the Pharmaceutical Kit of the Present Disclosure:

In this study, 22 breast cancer patients treated with surgery, scheduled for chemotherapy were included. Out of these, 16 patients were given additional pharmaceutical compositions of the kit mentioned hereinabove (Group 1—Study group), whereas remaining 6 patients were not provided with any additional pharmaceutical compositions of the kit of the present disclosure (Group 2—Control group). The stage and grade of the disease were matched for both Group 1 and Group 2. Pharmaceutical compositions of the kit were given from start of chemotherapy till one month after completion of chemotherapy, by which time acute adverse effects of chemotherapy are known to subside.

Inclusion Criteria for Enrolling Patients in this Study

Female patients: Age group between 25-75 years operated for breast cancer, who were in Stage I, or II or III of the disease and was eligible for chemotherapy.

Exclusion Criteria for Enrolling Patients in this Study

Patients who were on other Ayurvedic drugs for breast cancer or any other ailment and patients with distant metastasis and recurrence.

Outcome Measures—Time Points for Assessment of Outcome Measures—

A—Before chemotherapy for clinical and basic laboratory investigations and for symptoms 1 week after $1^{st}$ cycle of chemotherapy B—Mid chemotherapy C—End of chemotherapy D—1 month post chemotherapy A. Clinical Investigations The Patients were Followed for:

Assessment of adverse effects clinically and graded using CTCAE 4.03 Version (scale of grade 1-5 with grade '0' denoting absence of symptom except for taste alteration where the grading is 1-2 and for fatigue is from 1-4). Lower scale denotes less severity of the symptoms.

Assessment of performance status using Karnofsky score (Grading for well-being on 0 to 100 scale, higher score denotes better performance).

Assessment of Quality of Life (QoL) using Questionnaire QLQ C30 (designed for all types of cancers) and BR 23 (specially designed for breast cancer patients) of EORTC determined on the basis of patients' own perspective about her well being.

QLQ C30 can be interpreted as—

1. Symptomatology (Symptom score)
2. Ability to perform routine activities (Functional score)
3. Overall well-being (Global score)

Karnofsky score and scoring for QoL are internationally accepted means of scoring symptoms and quality of life for cancer patients used in various studies in clinical trials.

To support the clinical observations, additional studies were conducted using clinical laboratory investigations and basic laboratory investigations as follows:

B. Clinical Laboratory Investigations:

These investigations were conducted for assessing haemoglobin status and various cell types in peripheral blood to assess the bone marrow toxicity. Toxicity for liver and kidney was assessed on the basis of corresponding enzyme levels. CA 15.3—a breast cancer specific tumour marker was studied to assess residual tumour burden. CRP levels were assessed as an indicator of initiation of inflammatory response.

The tests performed were

Haemogram

LFT (Liver Function Test)

KFT (Kidney Function Test)

Tumor marker CA 15.3

CRP (C-reactive protein test)

C. Basic Laboratory Investigations:

These tests were carried out to provide proof of concept by assessing status of oxidative stress and immunomodulatory effect in these patients. Oxidative stress involves production of reactive oxygen species (ROS) which can be reduced by several enzymes and proteins acting in stepwise fashion. The level of oxidative stress was assessed with the help of two enzymes and one protein as representative candidates in the cascade of oxidative stress. Cytokines are the key molecules controlling proliferation, differentiation, and functions of immune cells and inflammatory response.

Immunological investigations—pro inflammatory cytokines—IL-1β, IL-6, IL-8 and IL-10 assessed by ELISA, using commercial kits.

Oxidative stress—Super oxide dismutase (SOD), Catalase and Glutathione assessed by biochemical methods, using commercial kits.

The data for biochemical investigations is represented as absolute values at each time point while for basic laboratory parameters and QLQ assessment, data was analyzed as fold change in a given parameter compared to its level at time point A.

For symptoms Mann Whitney Z test and for scores and basic and clinical laboratory investigations paired T test were applied. In addition, for symptoms the data was also analyzed based on the percentage and number of patients with varied severity levels of adverse effects at each time point.

Experiment 1: Alleviation of Adverse Effects of Chemotherapy in Breast Cancer Patients Using Pharmaceutical Kit of the Present Disclosure Out of commonly observed adverse effects, 8 significant symptoms were recorded in this study on the scale of grade 1-5 with grade '0' denoting absence of symptom (except for taste alteration where the grading is 1-2 and for fatigue is from 1-4). The mean of gradation at each time point was recorded for both the groups. The observations for each group were compared with respective time point A (After 1 cycle of chemotherapy, since chemotherapy induced adverse effects show up after chemotherapy starts), and fold change histograms were plotted (FIG. 1A to FIG. 8A). Therefore, status of symptoms at time point A was also plotted as zero fold change.

In second group of histograms (FIG. 1B to FIG. 8B), percentage and number of patients in no/low degree of adverse effects (grade 0 and 1 of symptoms) and higher degree of adverse effects (grade 2, 3, 4 and 5 of symptoms, where 5 is death of the patient) were represented in both the groups at various time points.

Figure 1A:
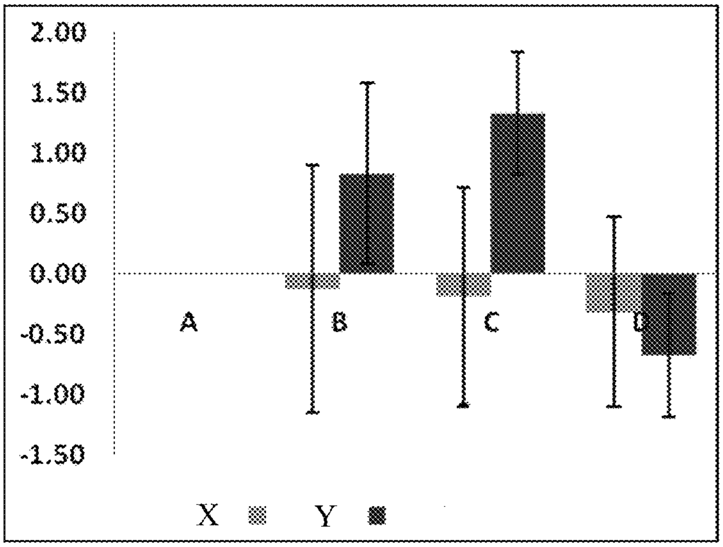
Figure 2A:
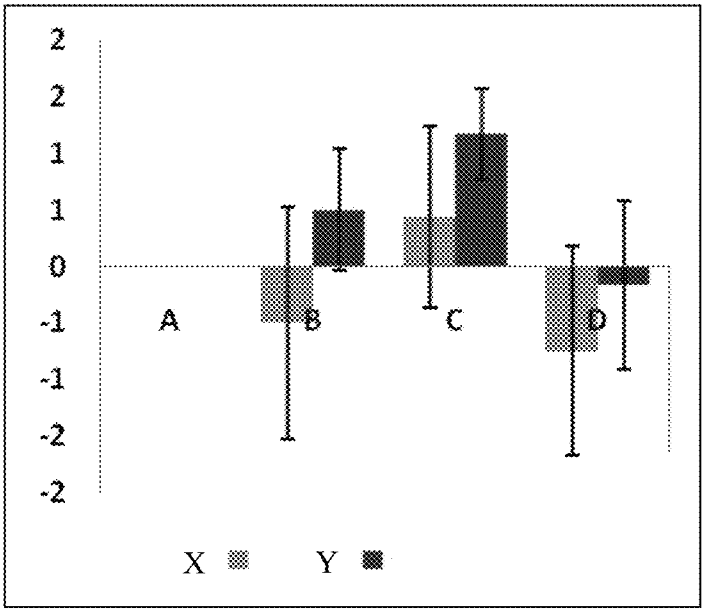
FIG. 2A and FIG. 2B depict the results of clinical investigation for nausea, wherein Study group is denoted by 'X' and Control group is denoted by 'Y'. Low degree adverse effect is denoted by 'P' and High degree adverse effect is denoted by 'Q' in FIG. 2B.

Results:

Anorexia and Nausea—Control group shows significant increase in anorexia (loss of appetite) and nausea during the period of chemotherapy (time points—B and C) in FIG. 1A and FIG. 2A. These 2 symptoms are significantly less in study group. Anorexia has p values of ($p=0.05$) and ($p=0.001$) at time points B and C, respectively, while nausea has p values of ($p=0.03$) and ($p=0.05$) at time points B and C, respectively.

Figure 1B:
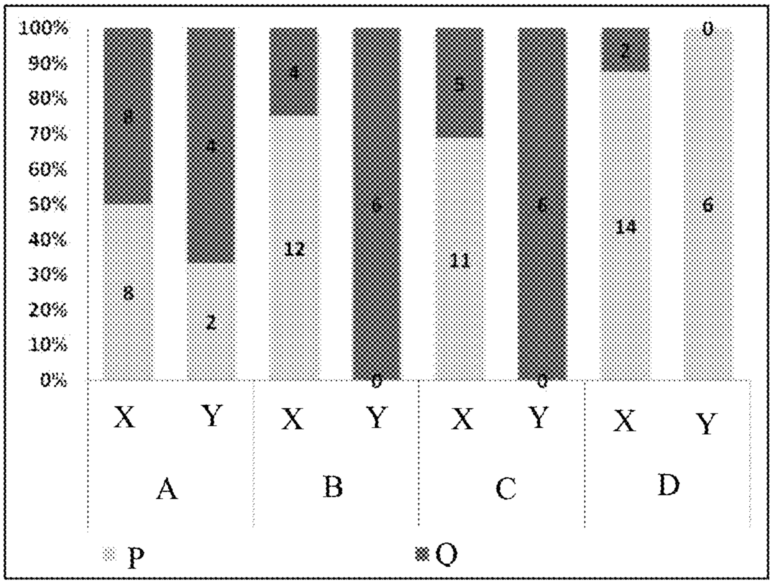
Figure 2B:
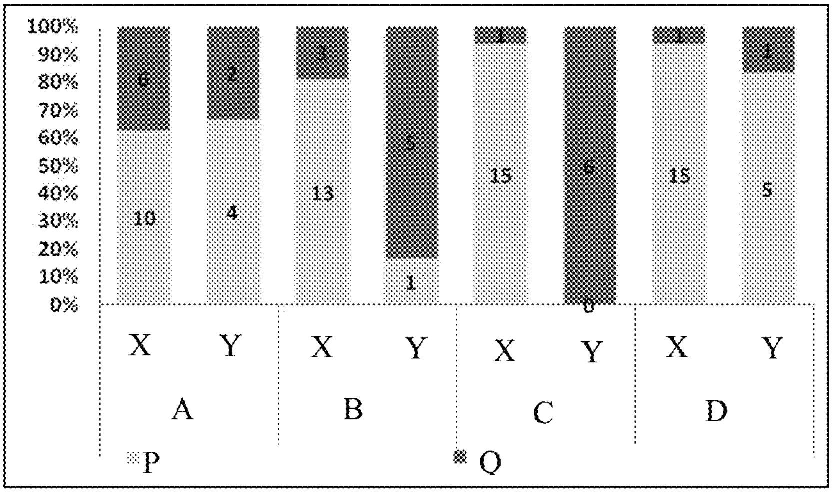

FIG. 1B and FIG. 2B show that at B and C time points, almost all the patients from control group suffered from anorexia and nausea in much higher degree than that of study group. This denotes that pharmaceutical composition of the kit of the present disclosure helped in maintaining good appetite and digestion during the course of chemotherapy.

Figure 3A:
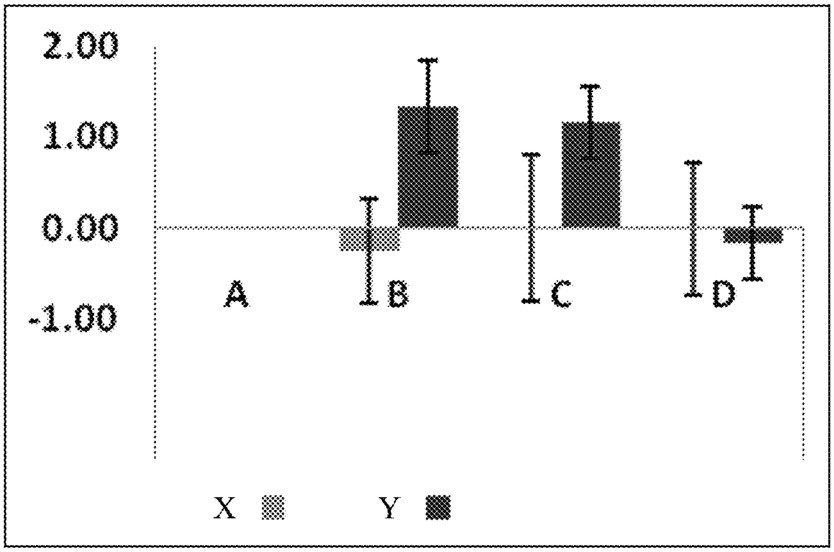
FIG. 3A and FIG. 3B depict the results of clinical investigation for vomiting, wherein Study group is denoted by 'X' and Control group is denoted by 'Y'. Low degree adverse effect is denoted by 'P' and High degree adverse effect is denoted by 'Q' in FIG. 3B.
Figure 3B:
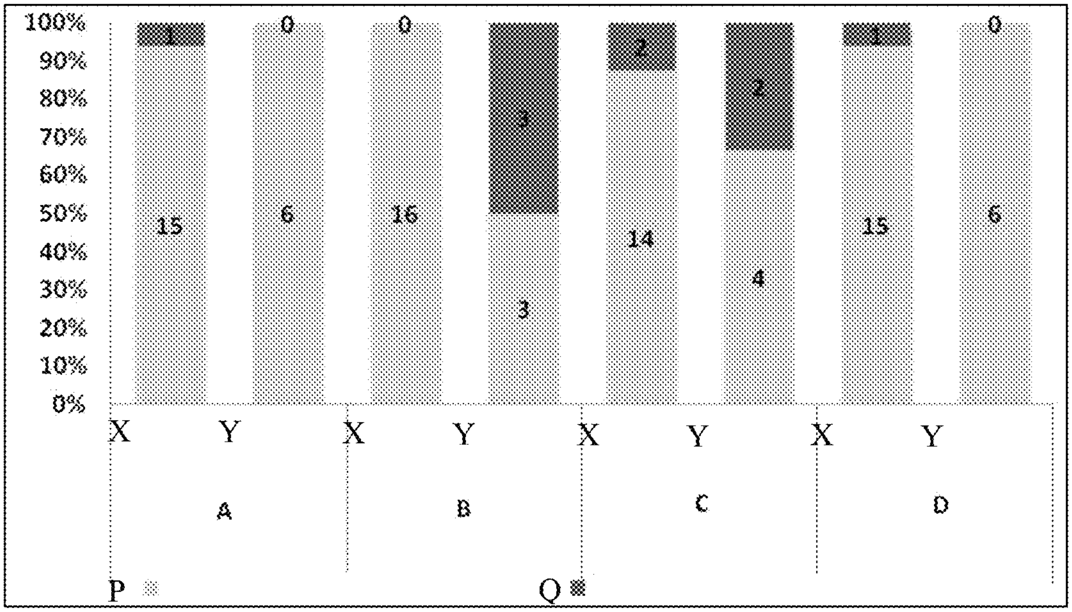

Vomiting—Control group shows significant increase in this symptom with p values of (p=0.0001) and (p=0.003) at time points B and C, respectively. While, vomiting is absent in study group patients at the same time points (FIG. 3A). As can be seen from FIG. 3B, at B and C time points nearly 50% and 30% patients, respectively in control group had much severe adverse effect of vomiting compared to that in the study group.

Figure 4A:
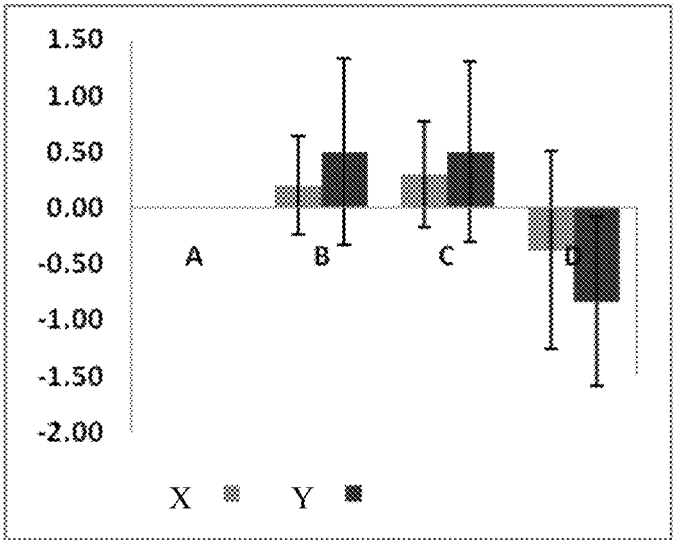
FIG. 4A and FIG. 4B depict the results of clinical investigation for constipation, wherein Study group is denoted by 'X' and Control group is denoted by 'Y'. Low degree adverse effect is denoted by 'P' and High degree adverse effect is denoted by 'Q' in FIG. 4B.
Figure 4B:
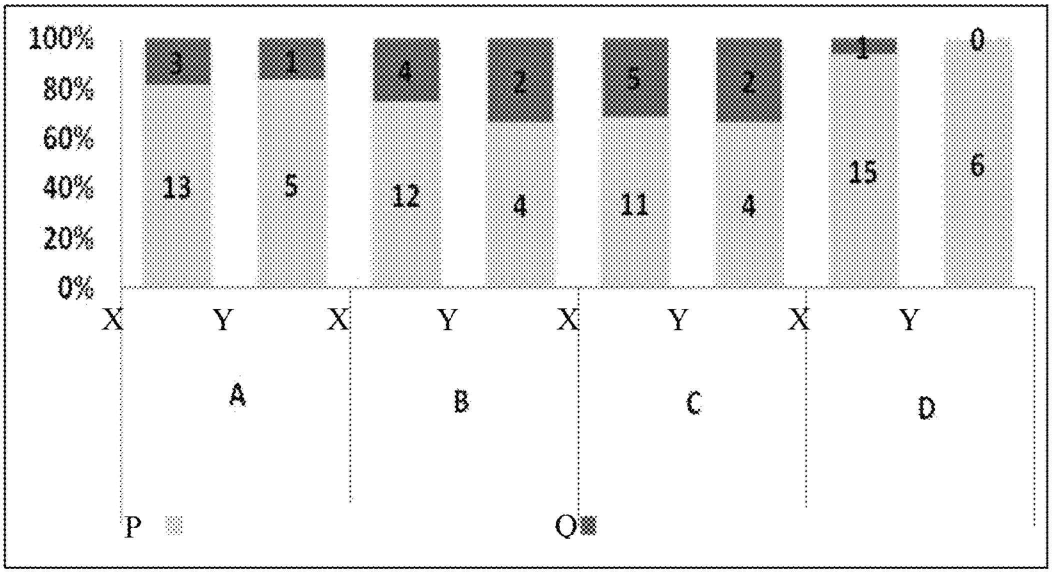

Constipation—This parameter did not show significant difference in both, the control and study group, however better outcome is observed in the study group compared to control group as can be seen from FIG. 4A and FIG. 4B.

Figure 5A:
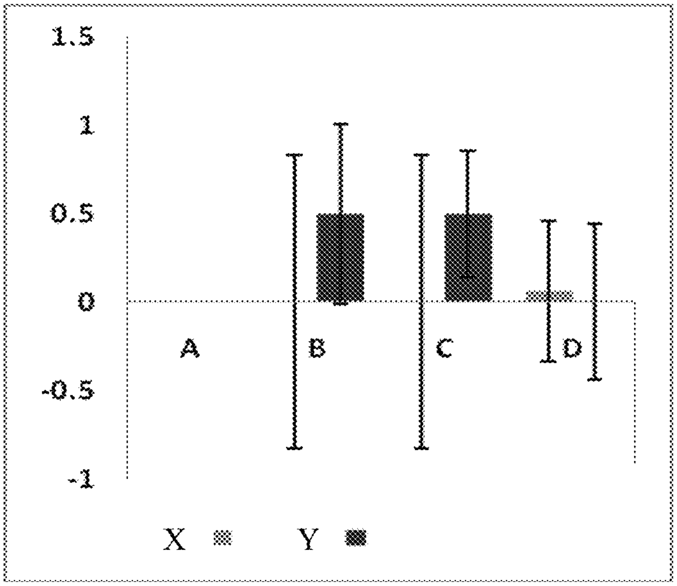
FIG. 5A and FIG. 5B depict the results of clinical investigation for fever, wherein Study group is denoted by 'X' and Control group is denoted by 'Y'. Low degree adverse effect is denoted by 'P' and High degree adverse effect is denoted by 'Q' in FIG. 5B.
Figure 5B:
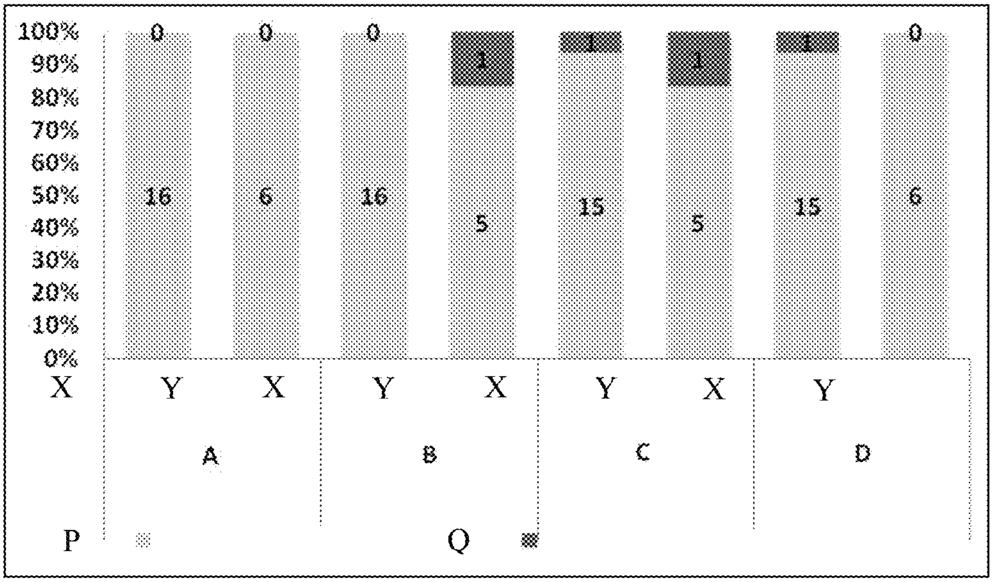

Fever and Taste Alteration—Fever is much pronounced in control group compared to study group patients in terms of fold increase (Figure SA), while in terms of percentage, no patient suffered from fever in study group during chemotherapy while at time point C and D, 1-1 patient at each time point had fever in control group (FIG. 5B).

Figure 6A:
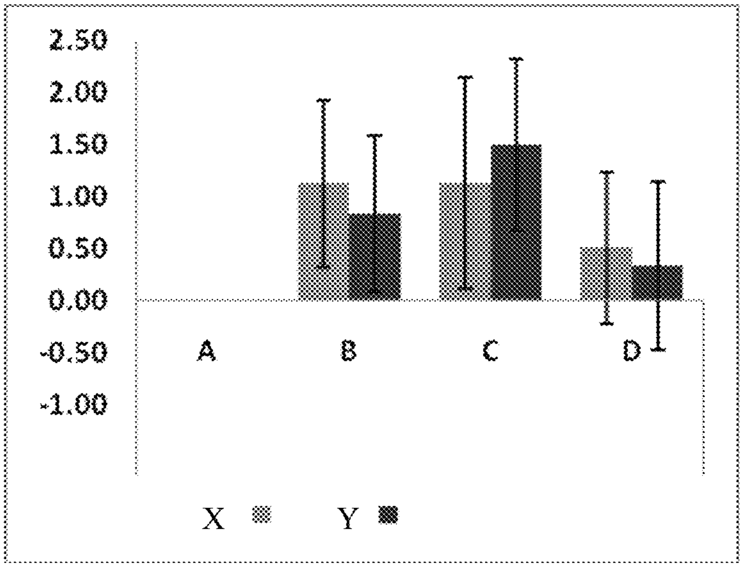
FIG. 6A and FIG. 6B depict the results of clinical investigation for taste alteration, wherein Study group is denoted by 'X' and Control group is denoted by 'Y'. Low degree adverse effect is denoted by 'P' and High degree adverse effect is denoted by 'Q' in FIG. 6B.
Figure 6B:
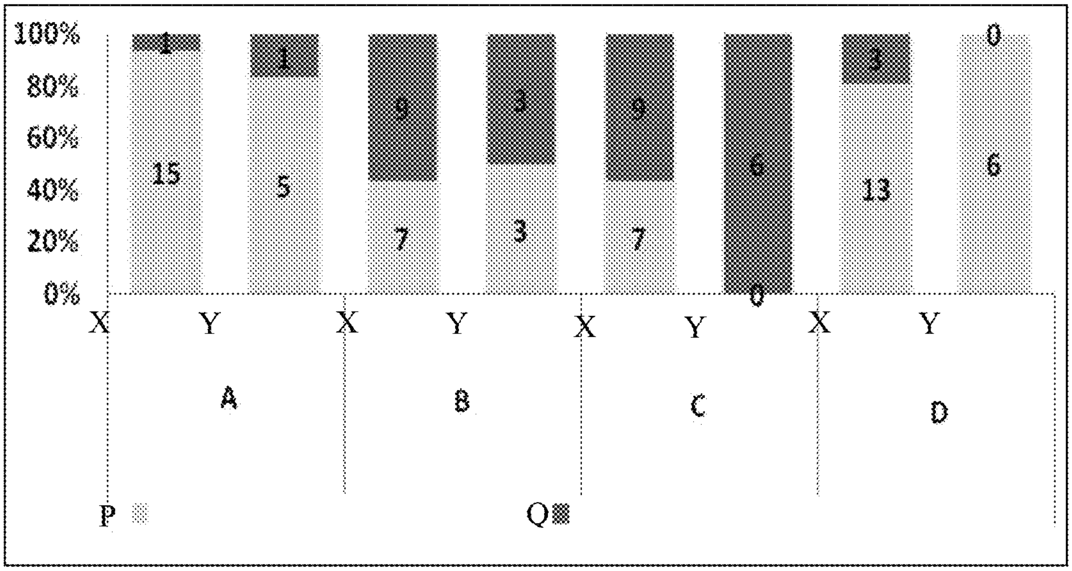
Figure 7A:
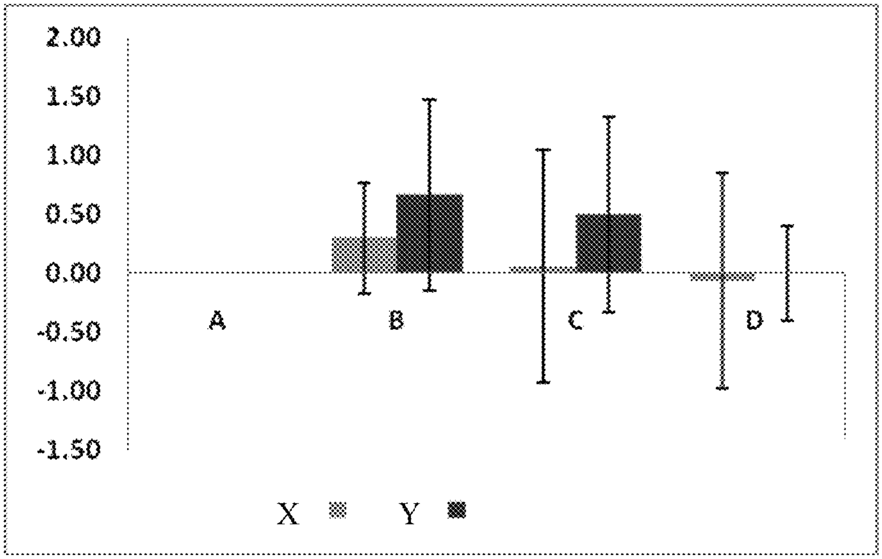
FIG. 7A and FIG. 7B depict the results of clinical investigation for mucositis, wherein Study group is denoted by 'X' and Control group is denoted by 'Y'. Low degree adverse effect is denoted by 'P' and High degree adverse effect is denoted by 'Q' in FIG. 7B.
Figure 7B:
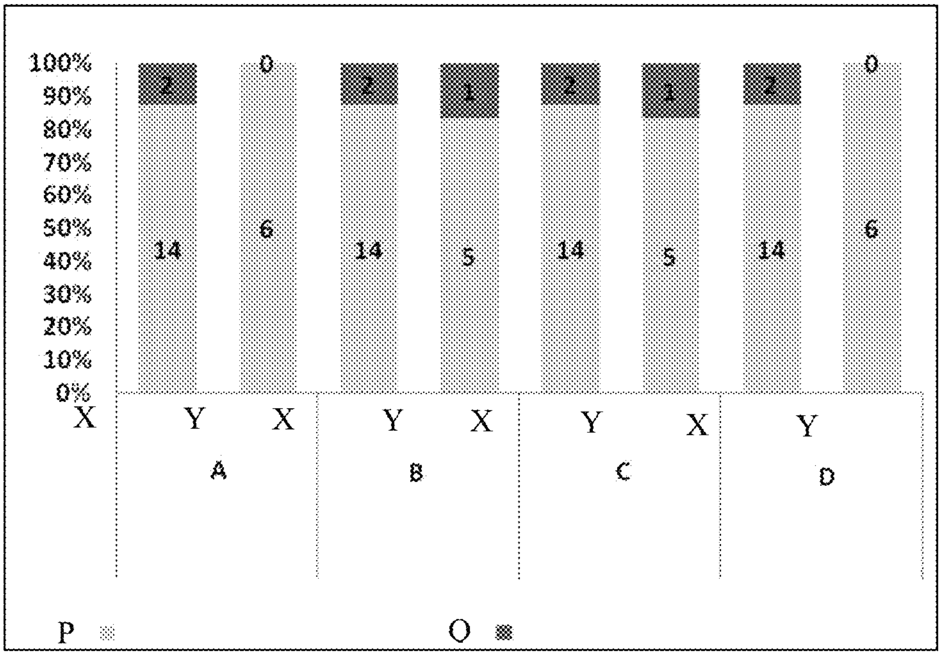

In case of taste alteration, there is no significant variation at any time point (FIG. 6A), but both groups suffered almost equally at time points A and B, while at the end of chemotherapy (i.e., at time point C) all control patients suffered from loss of taste (FIG. 6B).

Mucositis—No difference between study group and control group is noticed for this symptom. Both study group and control group patients have same degree of mucositis at all time points as per FIGS. 7A and 7B.

Figure 8A:
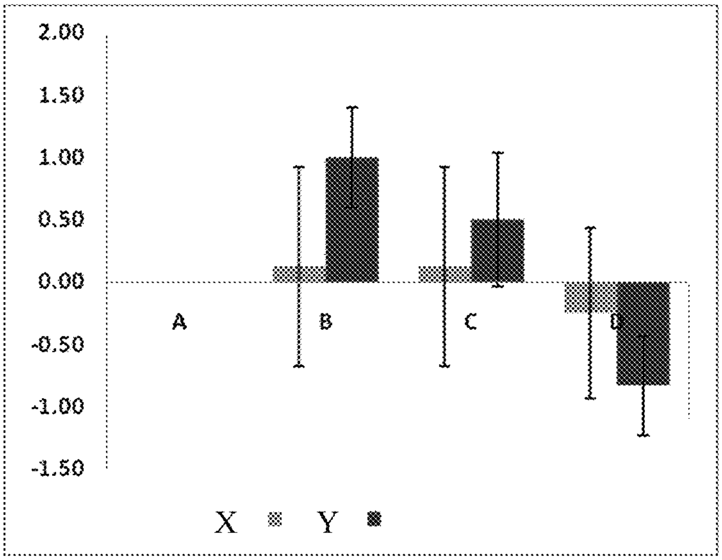
FIG. 8A and FIG. 8B depict the results of clinical investigation for fatigue, wherein Study group is denoted by 'X' and Control group is denoted by 'Y'. Low degree adverse effect is denoted by 'P' and High degree adverse effect is denoted by 'Q' in FIG. 8B.

Fatigue—At mid time point of chemotherapy (time point B and C) there is remarkable reduction in fatigue in study group compared to control group. Fatigue has p value of (p=0.007) at time point B in favor of study group (FIG. 8A). At the end of one month after chemotherapy (time point D) the trend remained the same but much less in control group.

Figure 8B:
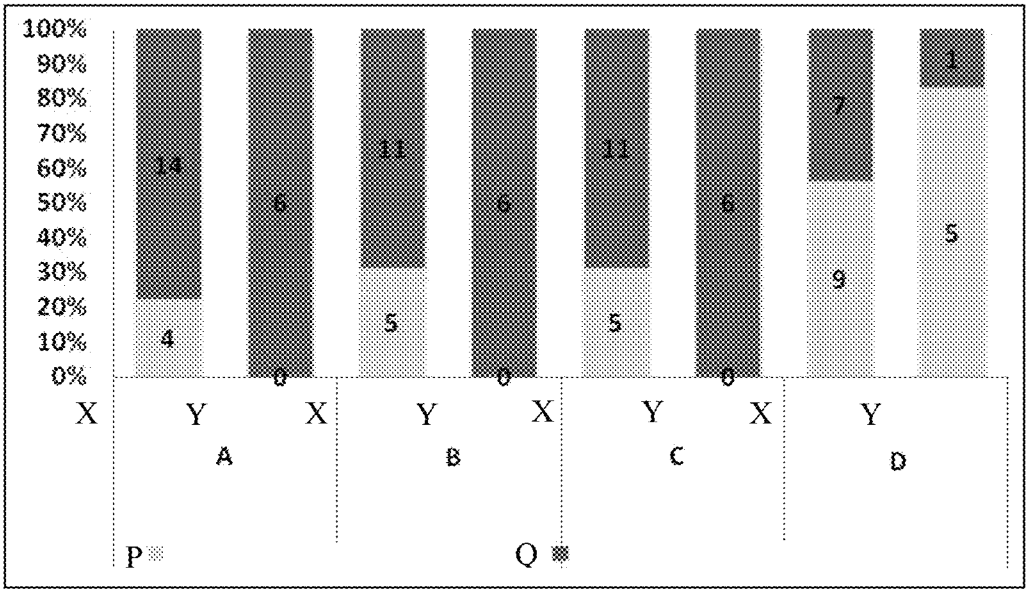

Fatigue is a symptom which can be managed well with the help of adjuvant pharmaceutical treatment during the course of chemotherapy (time points A, B and C) as revealed by 100% patients from control group suffering from higher degree of fatigue during chemotherapy (FIG. 8B). All patients of control group suffered from fatigue while about 20-30% patients from study group did not show fatigue during chemotherapy.

Experiment 2: Efficacy Studies of the Pharmaceutical Kit of Present Disclosure Using Haematological and Biochemical Parameters The clinical laboratory parameters studied were Haemogram, LFT, KFT, CRP, and tumour marker CA15.3. All these parameters were within normal range. Given below were the trends of differences between study and control groups. The results are based on mean values at each time point.

Figure 9:
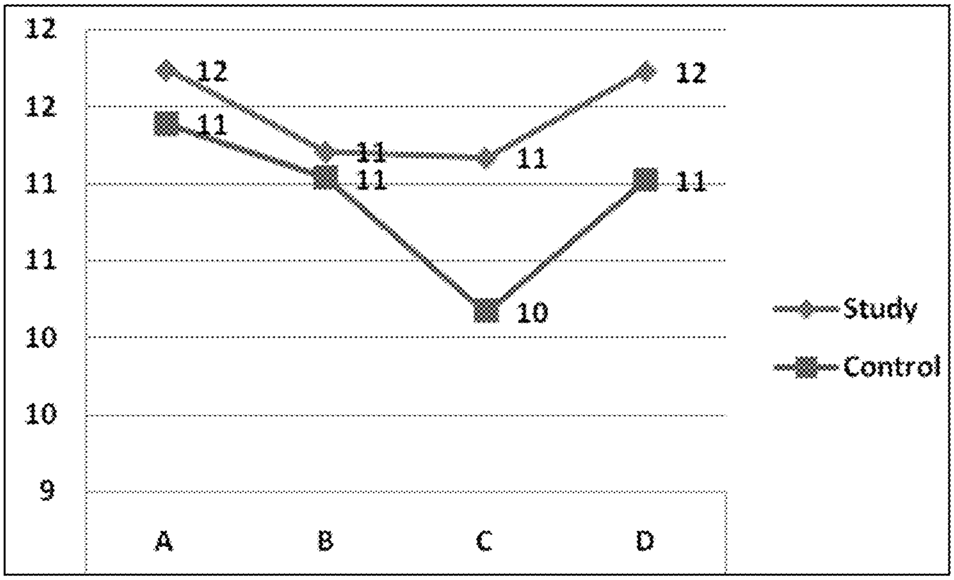
FIG. 9 depicts a graphical representation of Haemogram showing haemoglobin level of Study group and Control group.

Result:

Haemoglobin—Haemoglobin is reduced at the end of chemotherapy in both groups. The control group show more severe reduction. In both the groups it reaches to original level after 1 month of chemotherapy (FIG. 9).

Figure 10:
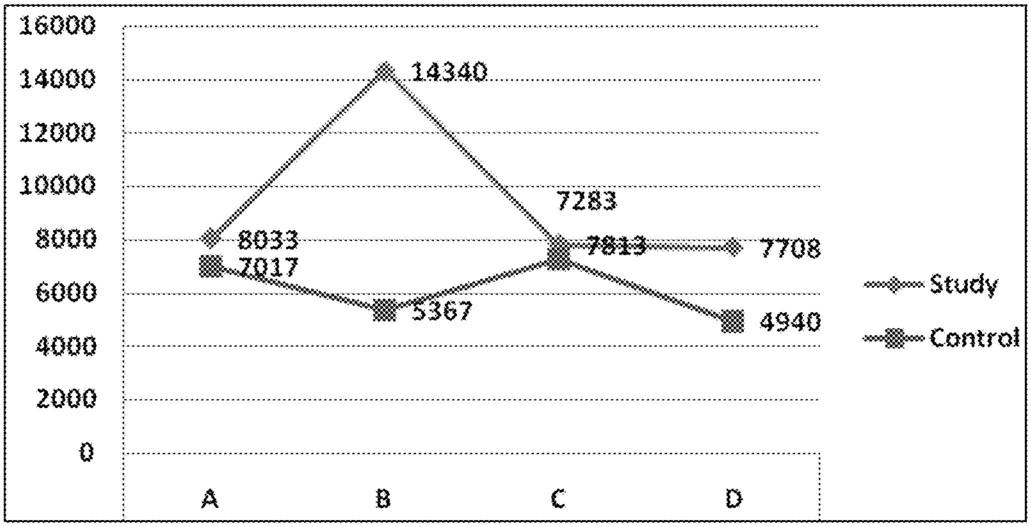
FIG. 10 depicts a graphical representation showing effect of chemotherapy on white blood cell (WBC) count of Study group and Control group.
Figure 11:
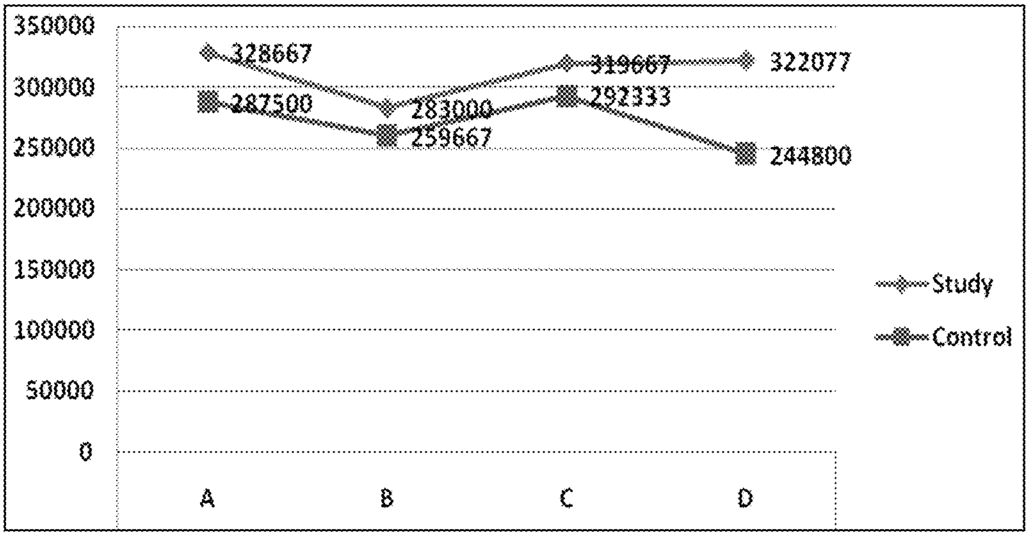
FIG. 11 depicts a graphical representation showing effect of chemotherapy on platelet count of Study group and Control group.

WBCs and Platelets—In study group WBCs show much increase at the mid time point of chemotherapy while control group shows stable WBC count at all the time points. Platelets do not show much variation in both the groups although patients of study group have higher count (FIG. 10 and FIG. 11).

Figure 12:
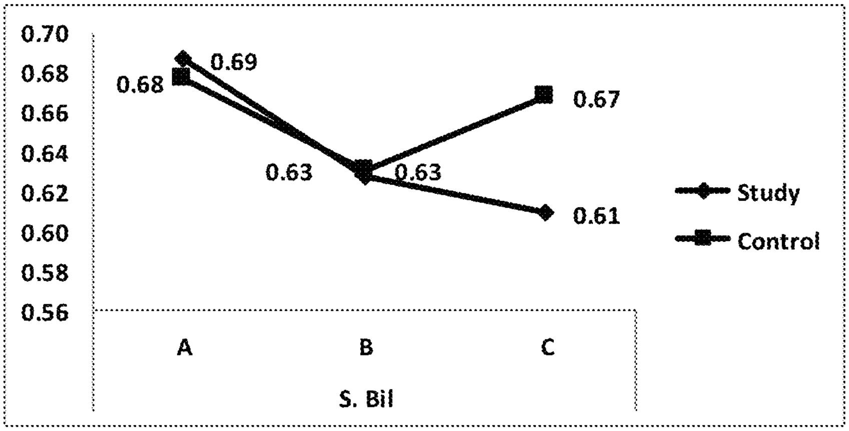
FIG. 12 depicts a graphical representation showing effect of chemotherapy on Serum Bilirubin level of Study group and Control group.
Figure 13:
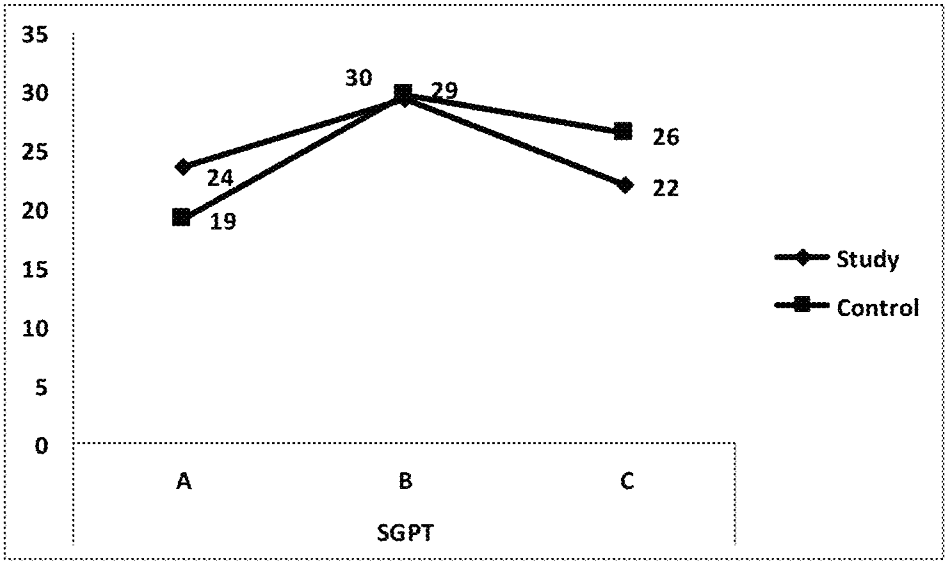
FIG. 13 depicts a graphical representation showing effect of chemotherapy on SGPT level of Study group and Control group.
Figure 14:
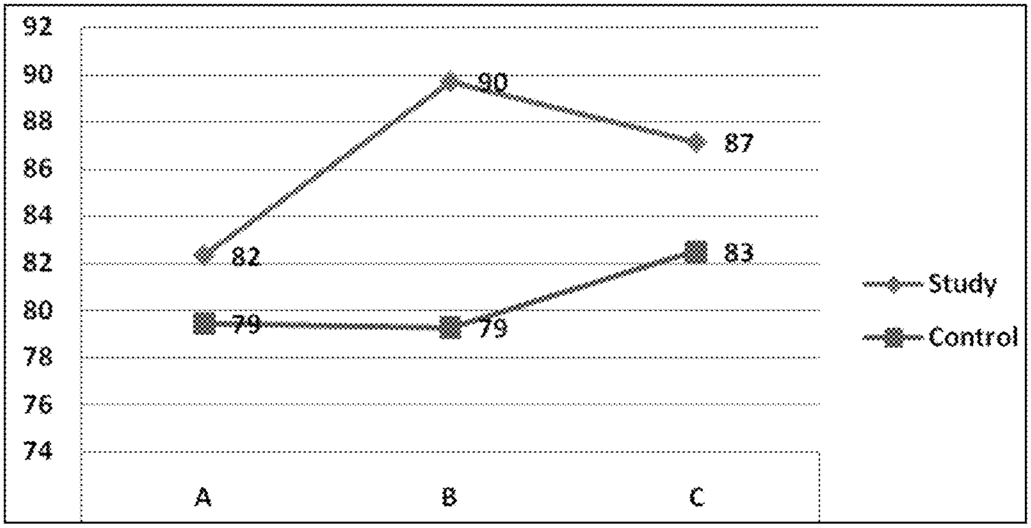
FIG. 14 depicts a graphical representation showing effect of chemotherapy on Serum Alkaline phosphatase level of Study group and Control group.

Serum Bilirubin—Levels of S. Bilirubin are comparable before commencement of chemotherapy in both groups. Control group shows considerable increase in serum bilirubin content as seen 1 month after chemotherapy in FIG. 12. While in study group the bilirubin values continue to show decrease throughout the study. Therefore, the liver function of patients from study group was not affected adversely. SGPT and Alkaline phosphatase levels are within normal range in both the groups throughout the study (indicating non toxicity of the pharmaceutical kit to the liver in the present disclosure) (FIG. 13 and FIG. 14).

Figure 15:
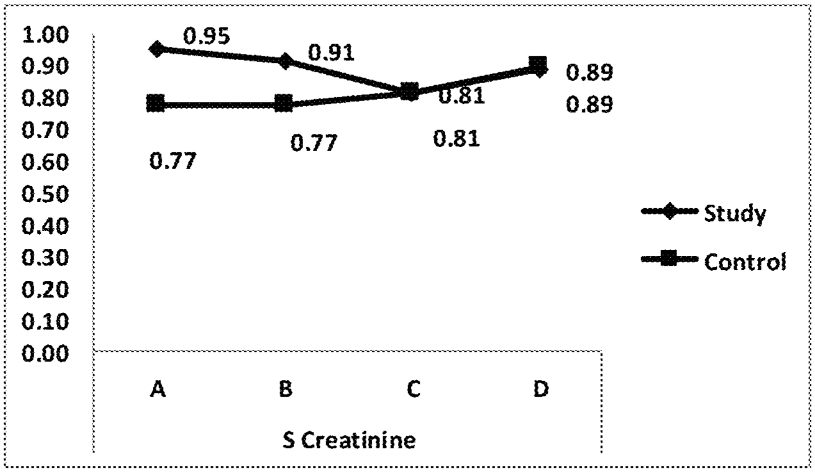
FIG. 15 depicts a graphical representation showing effect of chemotherapy on Serum Creatinine level of Study group and Control group.

Serum Creatinine—S. Creatinine level appears to increase in control group while in study group the creatinine level reduces during chemotherapy (FIG. 15). This data also suggest that the pharmaceutical kit of the present disclosure have not affected adversely the renal function of the patients.

The above results clearly indicate non toxicity of the pharmaceutical kit to liver and kidney functions.

Figure 16:
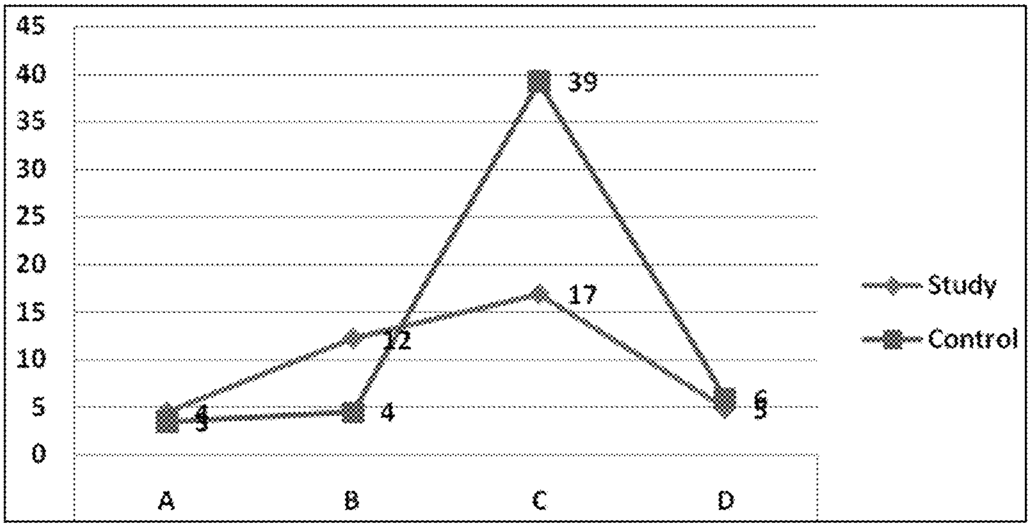
FIG. 16 depicts a graphical representation showing effect of chemotherapy on CRP (C—reactive protein) level of Study group and Control group.

CRP—CRP level is comparable before commencement of chemotherapy and is within normal range. During chemotherapy the CRP increases in both the groups. The increase is much higher in control group than that of study group indicating control of initiation of inflammatory activity because of treatment with the pharmaceutical kit of the present disclosure. At the end of chemotherapy in both the groups, the CRP levels came back to normal (FIG. 16).

Figure 17:
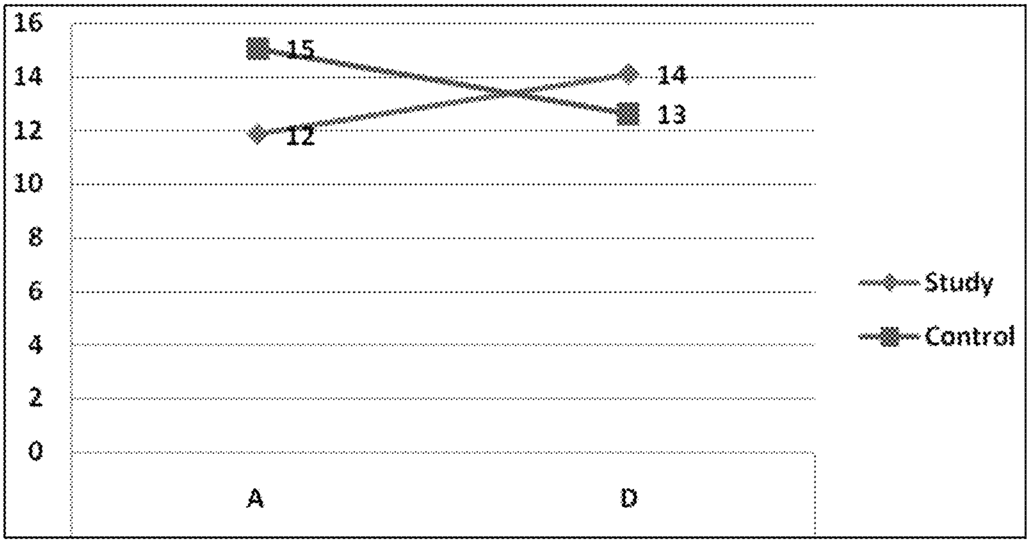
FIG. 17 depicts a graphical representation showing effect of chemotherapy on level of CA15.3 of Study group and Control group.
Figure 18:
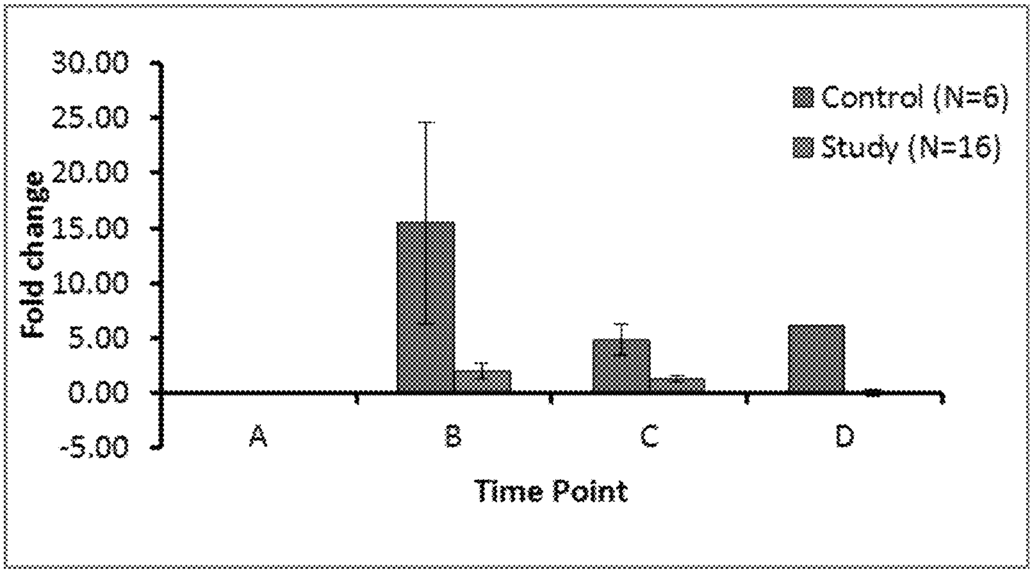
FIG. 18 depicts a graphical representation showing effect of chemotherapy on IL-1β (Interleukine-1β) level as fold change in Study group and Control group.
Figure 19:
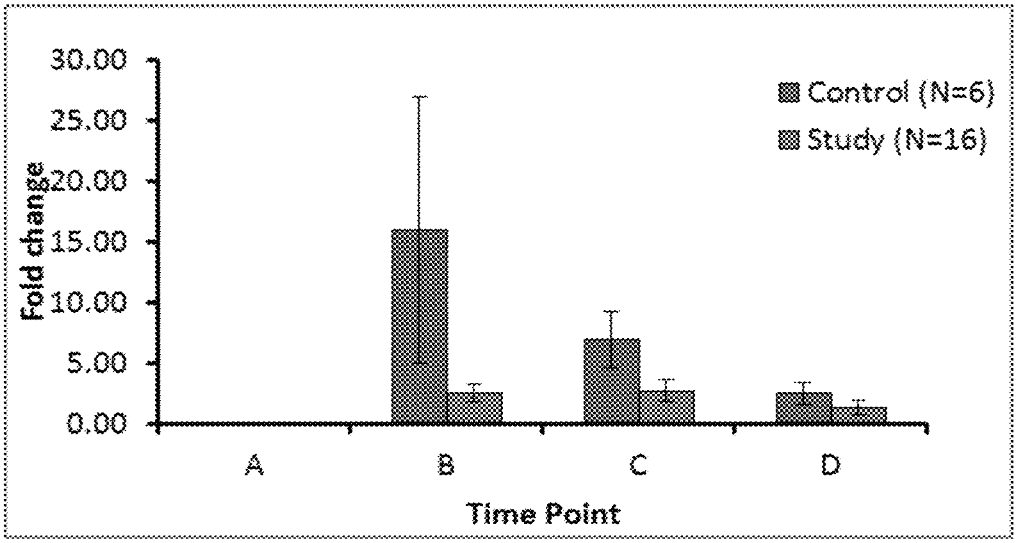
FIG. 19 depicts a graphical representation showing effect of chemotherapy on IL-6 (Interleukine-6) level as fold change in Study group and Control group.
Figure 20:
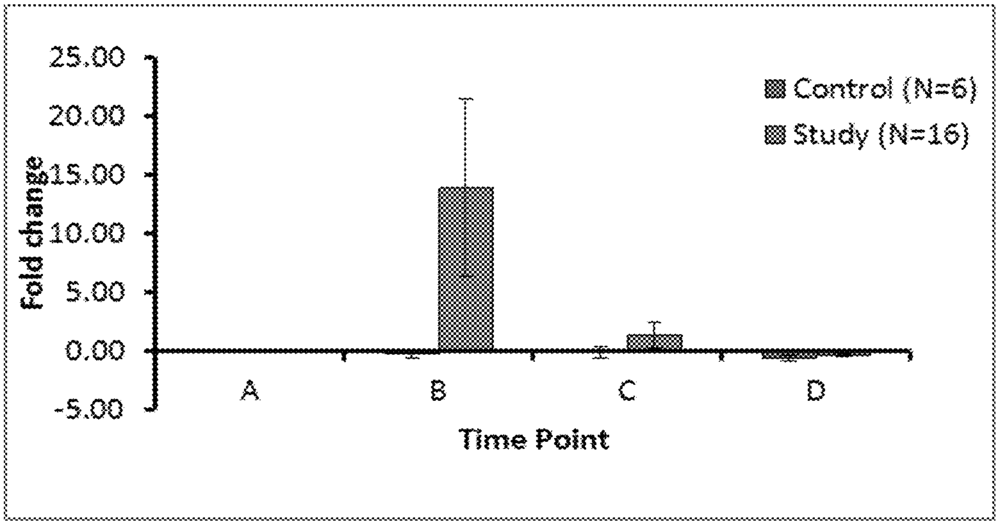
FIG. 20 depicts a graphical representation showing effect of chemotherapy on IL-10 (Interleukine-10) level as fold change in Study group and Control group.
Figure 21:
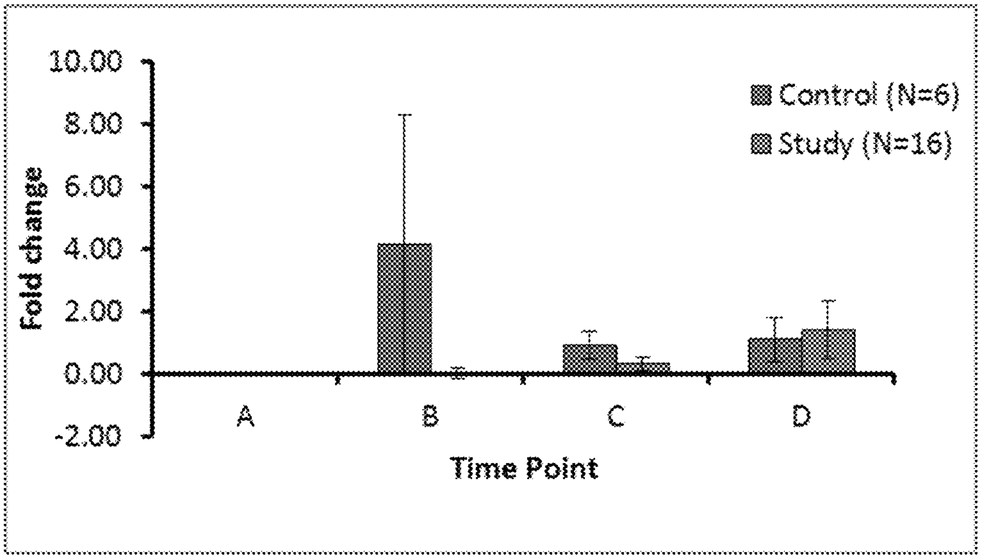
FIG. 21 depicts a graphical representation showing effect of chemotherapy on IL-8 (Interleukine-8) level as fold change in Study group and Control group.

CA15.3—Level of CA15.3 is less than or comparable to normal level in both the groups. This could be because of reduced tumour load secondary to surgery (FIG. 17).

Experiment 3: Studies on Immunomodulatory and Anti-Oxidant Markers Using Pharmaceutical Kit of the Present Disclosure Result:

Immunomodulatory markers: As stated before, levels of pro-inflammatory cytokines IL-1β, IL-6, IL-8, and IL-10 were assessed to see the pro-inflammatory response caused by chemotherapy. The levels were represented in the form of fold increase at respective time points.

It was seen that all the inflammatory cytokines increased up to 15 fold during chemotherapy in control group. The inflammatory response was much less in study group. At time point D (one month after last chemotherapy cycle) the level of IL-1β, IL-8, and IL-10 are still higher in control group patients compared to study group patients (FIG. 18 to FIG. 21).

Figure 22:
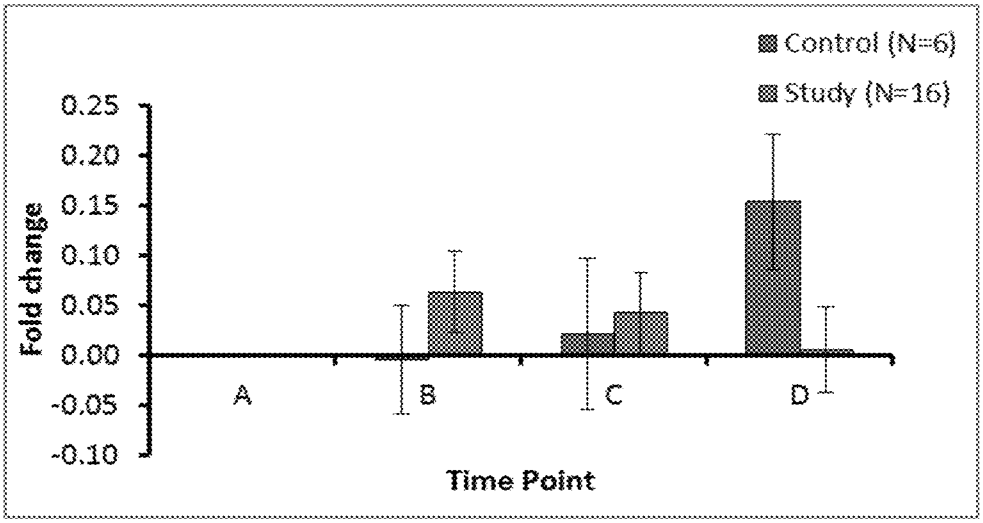
FIG. 22 depicts a graphical representation showing effect of chemotherapy on SOD (Superoxide dismutase) activity as fold change in Study group and Control group.
Figure 23:
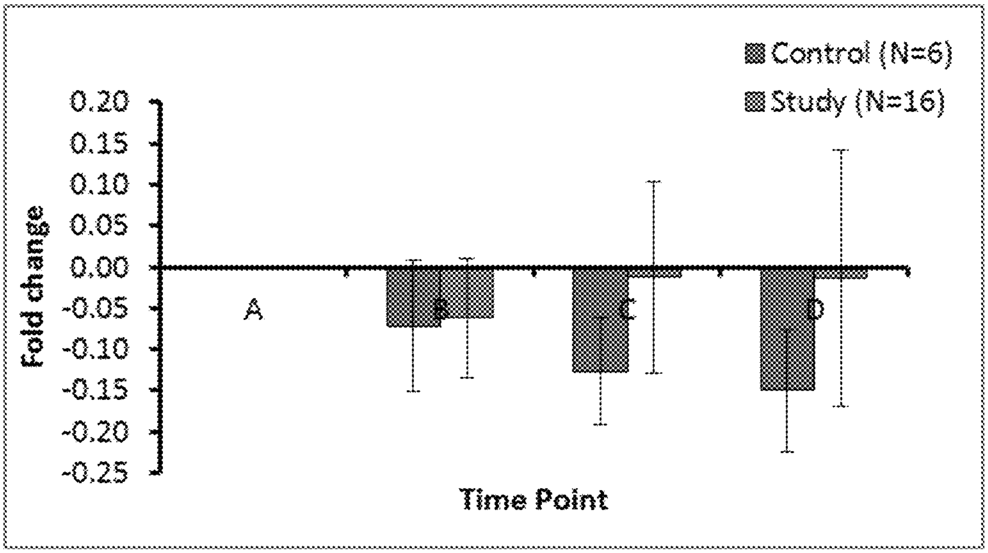
FIG. 23 depicts a graphical representation showing effect of chemotherapy on catalase activity as fold change in Study group and Control group.
Figure 24:
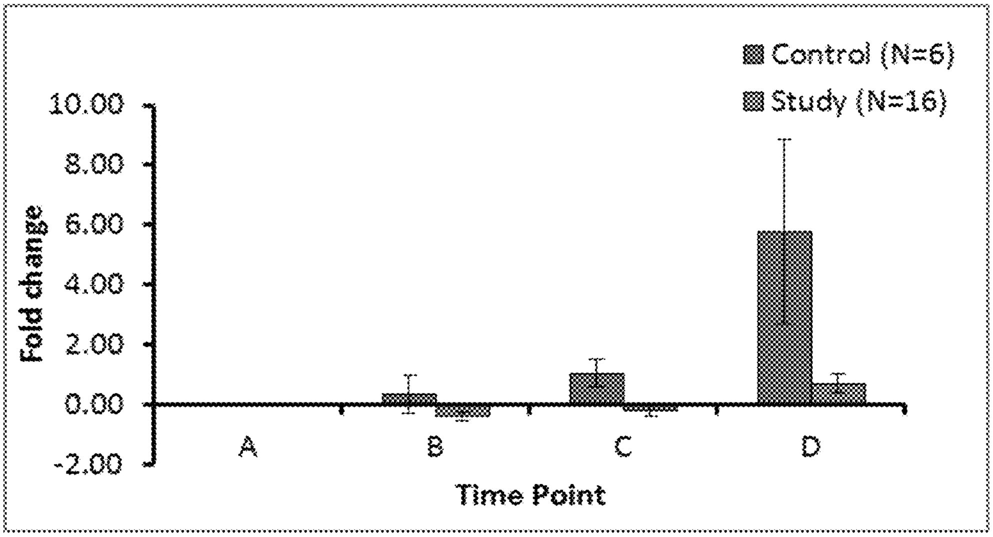
FIG. 24 depicts a graphical representation showing effect of chemotherapy on glutathione level as fold change in Study group and Control group.

Oxidative Stress Markers:

Result:

The parameters for oxidative stress are activity of enzymes such as SOD and catalase, and the concentration of ultimate essential protein glutathione. It is seen that, SOD enzyme showed progressive reduction at time points B, C, and D in the study group. While, the control group continued to show increase in SOD levels (FIG. 22). Apparently, catalase activity is less in both the groups. The trend shows that during the course of chemotherapy, there is further reduction in catalase activity at time points B, C, and D in the study group. While, the reduction in catalase activity is more pronounced in the control group (FIG. 23). Glutathione, which is low at time points B and C, shows increased levels 1 month after chemotherapy in the study group. Whereas, glutathione level in control group increases considerably during progression of chemotherapy and 1 month thereafter (FIG. 24). From FIGS. 22 to 24, it is evident that dis-mutation of Reactive Oxygen Species i.e. superoxide ($O_2^-$) into hydrogen peroxide and later decomposition to oxygen are efficient in the study group due to the use of the pharmaceutical kit as compared to the control group. It is further confirmed by increased levels of Glutathione in the control group as compared to the study group.

Experiment 4: Assessment of Quality of Life Using Pharmaceutical Kit of the Present Disclosure Karnofsky score—Karnofsky score was recorded on 0-100 scale, the score of 100 showing normal performance status. To represent this score in graphs, the mean values at each time point were recorded for both the groups. These values were represented as actual scores in FIG. 25A and fold change in FIG. 25B.

Figure 25A:
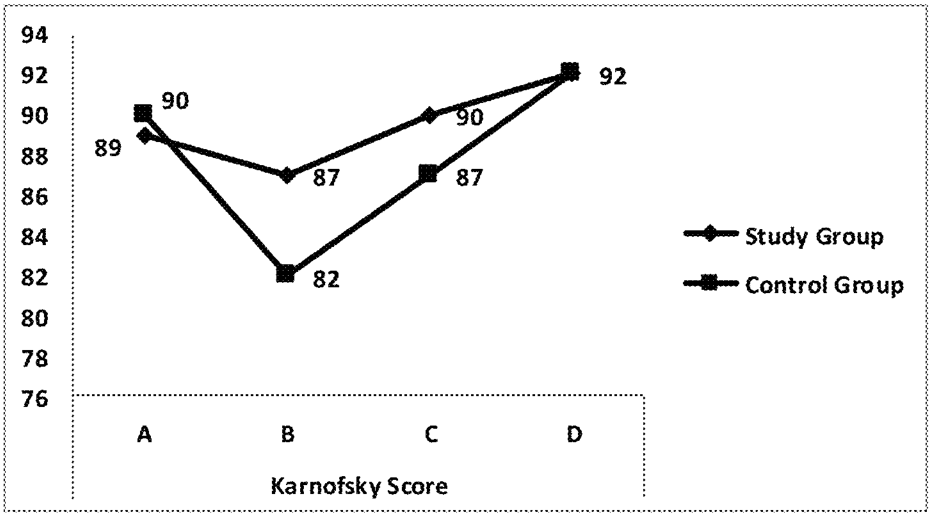
FIG. 25A and FIG. 25B depict the results of clinical investigation for actual Karnofsky score and fold change respectively.
Figure 25B:
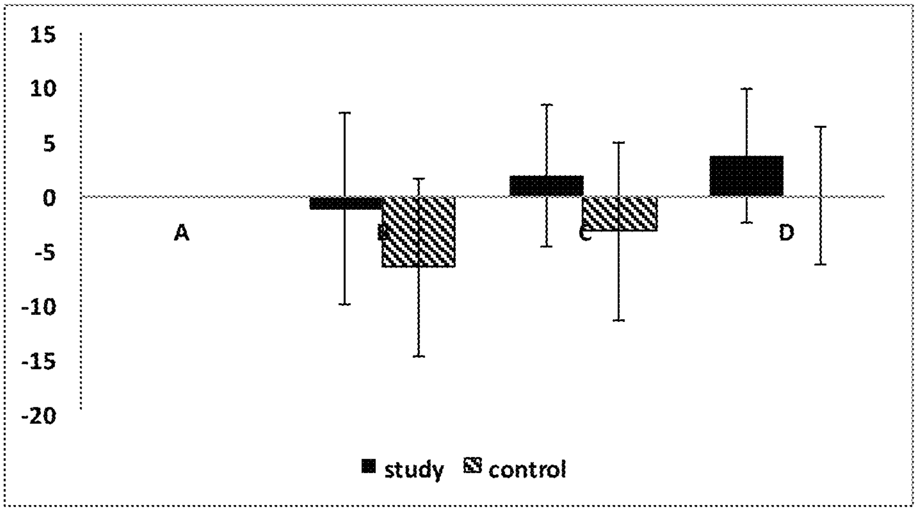

As seen from absolute score, it is comparable before commencement of chemotherapy in both the groups. Control group shows considerable reduction in the score in the middle of the chemotherapy at time point B and C (FIG. 25A). Scores of both the groups show increase at the end of chemotherapy. Similar trend is also seen in fold change diagram (FIG. 25B).

QLQ Scores

QLQ scores are recorded as per the questionnaires (QLQ C 30 and BR 23) as—

1. Functional score (recommended from questionnaire C 30)
2. Symptom score (recommended from questionnaire C 30)
3. Global score (recommended from questionnaire C 30)
4. Breast score (BR 23)

The mean score values at each time point were recorded for both the groups (Line graph).

Figure 26A:
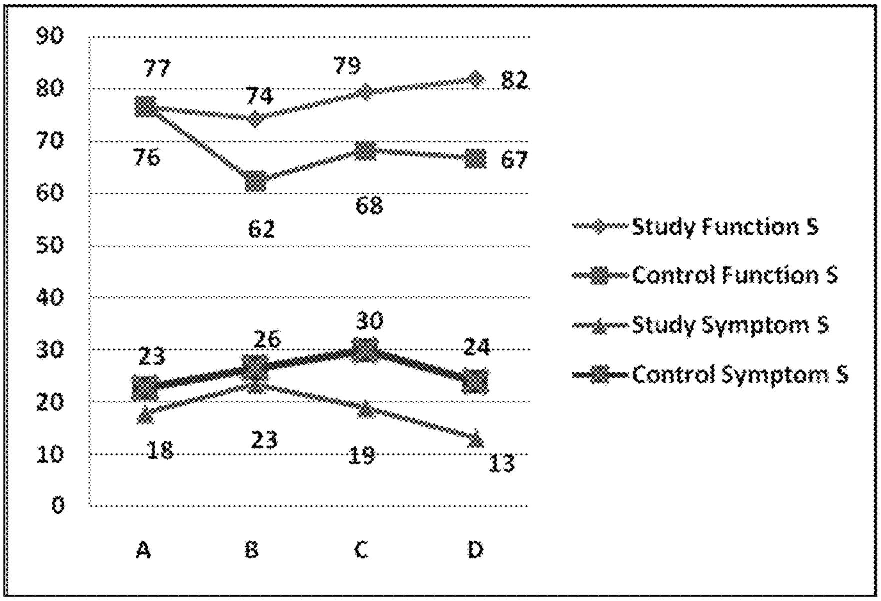
FIG. 26A depicts a graphical representation for Functional score and symptom score for both Study group and Control group.

Results:

The functional score is higher at all the stages in the study group indicating maintenance of good functions with p value of 0.04 at the time point D (FIG. 26A). The symptom scores in study group show low values indicating reduction in symptoms.

Figure 26B:
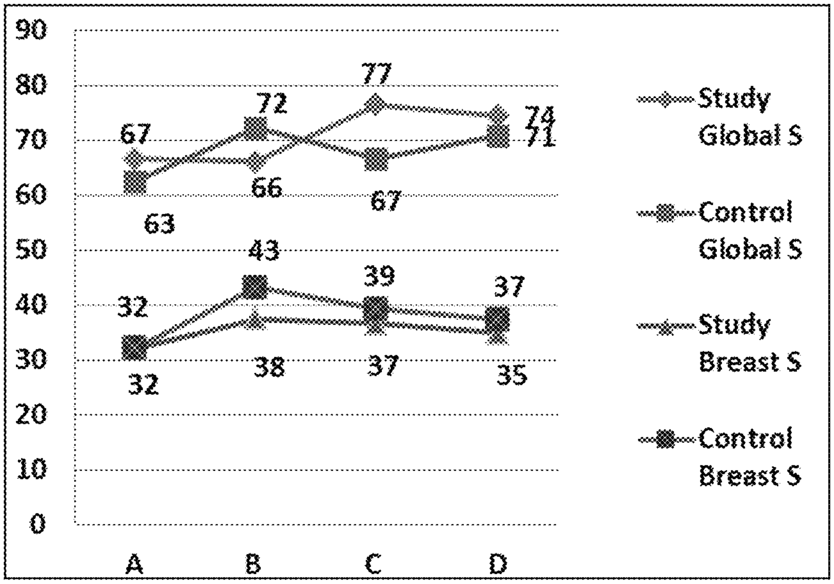
FIG. 26B depicts a graphical representation for Global score and Breast score for both Study group and Control group.

The global and breast scores do not show difference in the control group and the study group at any of the time points (FIG. 26B).

Example 3

Case Reports of Two Patients Matched for Age, Stage, Grade and ER-PR Status: One Treated with the Pharmaceutical Kit of the Present Disclosure (Case Report 1) and One not Treated with the Pharmaceutical Kit of the Present Disclosure (Case Report 2)].

Eleven symptoms viz., anorexia, constipation, diarrhoea, taste alteration, fever, fatigue, nausea, vomiting, mucositis, dyspepsia, and dyspnea were assessed in both the case reports along with weight. Assessment time points and remaining outcome measures for both the case studies are similar to those as explained in example 2.

Case Report 1:

Patient Information:

Age at diagnosis: 40 yrs.

Diagnosis: Ca Breast—Left

Status at enrollment: Post-Operative

Date of diagnosis: 31 May 2016

Histopathology report: Infiltrating Duct Carcinoma

Stage: III, T2 N1 M0

Grade: III

Immunohistochemistry (IHC): Estrogen receptor (ER), Progesterone receptor (PR), Her2 neu receptor—Negative (Triple Negative Breast Cancer)

Marital status: Married at the age of 18 yr with 2 children

Past medical/surgical history: Tubectomy done in 1998.

History of familial cancer: Mother—Ca Colon, Maternal Uncle-Leukemia

Treatment Details—

Surgery: Left Breast MRM with axillary node dissection done on 16 Jul. 2016 at a hospital in Pune.

Chemotherapy Details: 4 cycles of Inj. Adriamycin 90 mg and Inj. Cyclophosphamide 900 mg taken from 31 Aug. 2016 to 2 Nov. 2016 followed by 4 cycles of Inj. Paclitaxel 260 mg from 23 Nov. 2016 to 25 Jan. 2017 at ICTRC.

Oral Treatment Using Pharmaceutical Kit (as Per Table 1) of the Present Disclosure Along With Chemotherapy Till 1 Month after the End of Chemotherapy:

Results:

1. Chemotherapy Side Effects—

Figure 27:
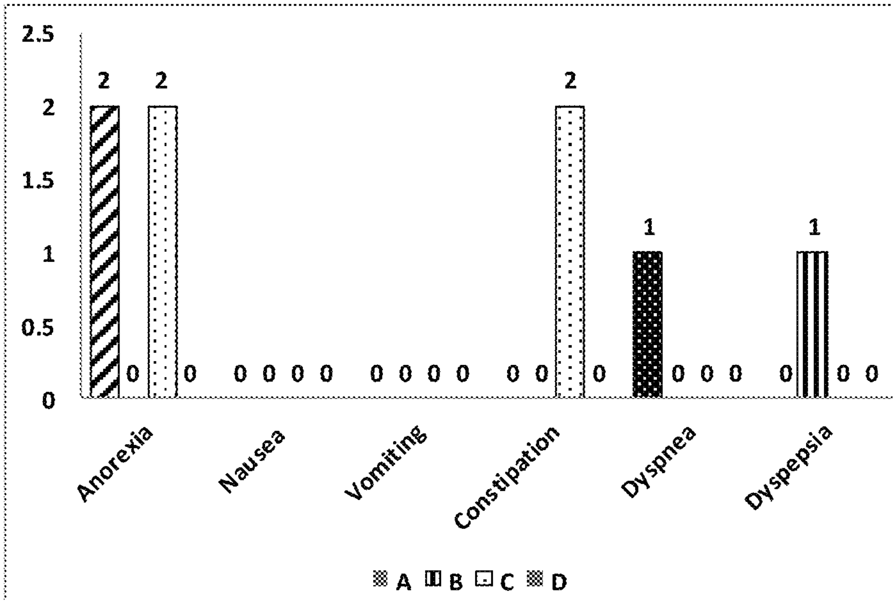
FIG. 27 depicts a graphical representation showing effect of chemotherapy on anorexia, nausea, vomiting, constipation, dyspnea and dyspepsia of the patient described in case report 1 (Study group patient)
Figure 28:
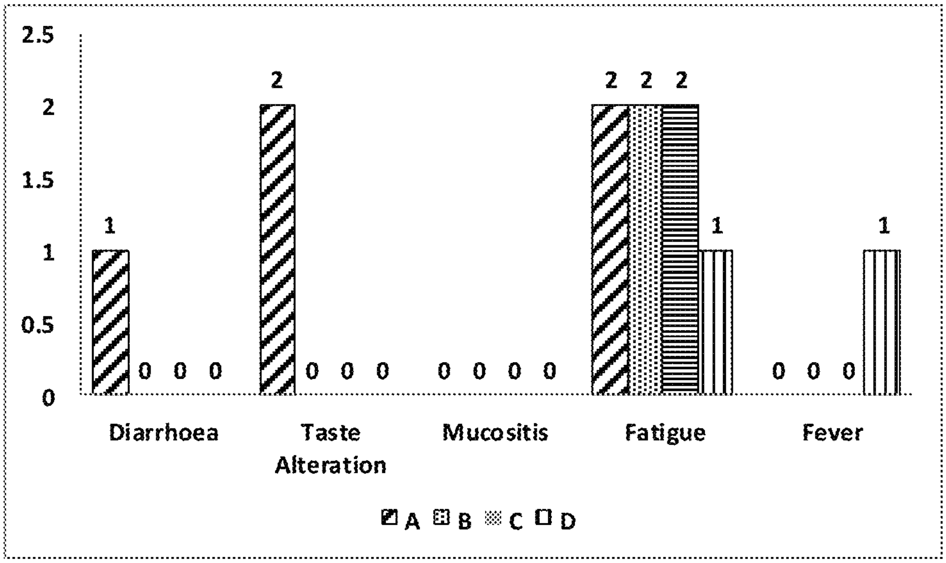
FIG. 28 depicts a graphical representation showing effect of chemotherapy on diarrhoea, taste alteration, mucositis, fatigue, and fever of the patient described in case report 1 (Study group patient)

Out of commonly observed adverse effects, 11 significant symptoms were recorded in this case report on the scale of 1-5 with grade '0' denoting absence of symptom (except for taste alteration where the grading is 1-2, for dyspepsia the grading is 1-3 and for fatigue is 1-4) and have been depicted in FIG. 27 and FIG. 28. Since adverse effects of chemotherapy are visible only after 1 cycle of chemotherapy, time point A is therefore recorded as values after 1 cycle of chemotherapy and all further points (from B to D) are compared with this time point A.

From FIG. 27 and FIG. 28, it is seen that immediate adverse effects shown by this patient are anorexia, constipation, diarrhoea, taste alteration, fever, and fatigue. While nausea, vomiting, and mucositis are absent. Dyspnea and dyspepsia which are also subsided.

The patient showed anorexia of grade 2 before and at the end of chemotherapy, diarrhoea as a very early response, constipation at the end of chemotherapy while taste alteration only as an early symptom. On the other hand, fatigue was evident till the end of chemotherapy which was reduced by 50% at time point D. Fever was observed only at the time point D. Dyspnea and dyspepsia which are present at A and B time point respectively subsided later.

These observations of rather quick relief from adverse effects can be attributed to the adjunct oral treatment using the pharmaceutical kit of the present disclosure during and after chemotherapy.

2. Haematological and Biochemical Analysis—

TABLE 6

Data on haematological and biochemical investigations.

| Time point | Hb *(12-16 g/dl) | WBC *(4000-11000/ cmm) | Platelet *(150000-450000/ cmm) | S. Bil *(0-1.2 mg/dl) | SGOT *(0-31 U/L) | SGPT *(0-32 U/L) | S. Alkaline Phosphates *(44-147 U/L) | S. Creatinine *(0.7-1.7 mg/dl) | CA 15.3 *(0-32 U/ml) | CRP *(0-6 mg/L) |
|---|---|---|---|---|---|---|---|---|---|---|
| A | 13.8 | 7800 | 318000 | 1.07 | 18.77 | 20.61 | 53.84 | 1.14 | 0.613 | 1.89 |
| B | 12 | 6200 | 241000 | 0.64 | 31.47 | 24.92 | 57.94 | 0.76 | ND | 0.78 |

TABLE 6-continued

Data on haematological and biochemical investigations.

| Time point | Hb *(12-16 g/dl) | WBC *(4000-11000/ cmm) | Platelet *(150000-450000/ cmm) | S. Bil *(0-1.2 mg/dl) | SGOT *(0-31 U/L) | SGPT *(0-32 U/L) | S. Alkaline Phosphates *(44-147 U/L) | S. Creatinine *(0.7-1.7 mg/dl) | CA 15.3 *(0-32 U/ml) | CRP *(0-6 mg/L) |
|---|---|---|---|---|---|---|---|---|---|---|
| C | 13.6 | 7000 | 421000 | 0.7 | 27.24 | 22.04 | 67.37 | 0.86 | ND | 2.09 |
| D | 13.1 | 9200 | 324000 | 0.68 | 33.47 | 30.11 | 70.42 | 0.84 | 11.673 | 7.72 |

*Denotes normal range of respective parameter.
ND—Not done
cmm—cubic millimeter

From table 6, it is evident that all the clinical laboratory parameters were in normal range at all time points.

Figure 29:
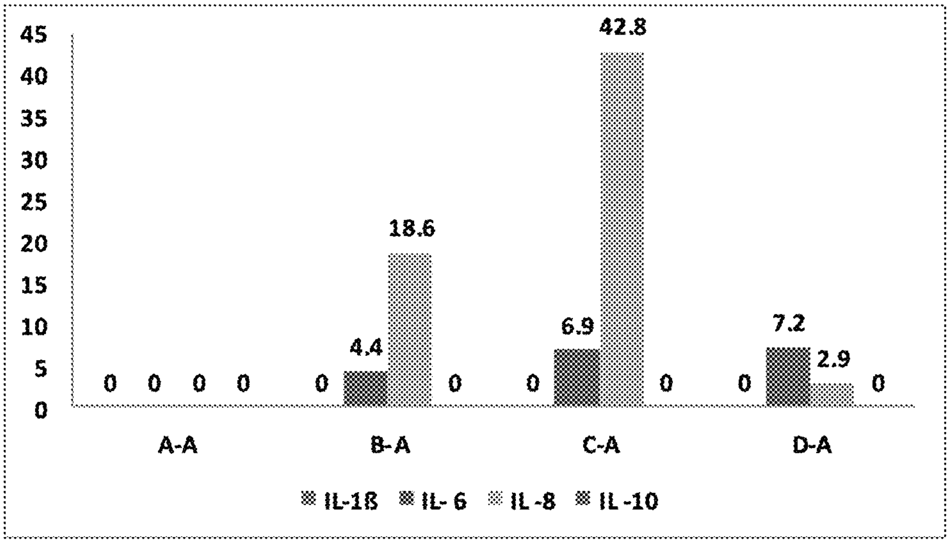
FIG. 29 depicts a graphical representation showing effect of chemotherapy on IL-1β, IL-6, IL-8, and IL-10 levels in pg/ml units of the patient described in case report 1 (Study group patient)

3. Immune and Oxidative Stress Status:

As for the cytokine response IL-1β and IL-10 are not detected, while potent pro-inflammatory cytokines IL-6 has increased during chemotherapy, and then remained stable thereafter, while IL-8 has increased significantly at time point C but decreased at time point D (FIG. 29). This indicates that although, there is continuation of pro-inflammatory activity till the end of chemotherapy, partial reduction in their activity towards the end of chemotherapy could be due to the pharmaceutical kit of the present disclosure.

Figure 30:
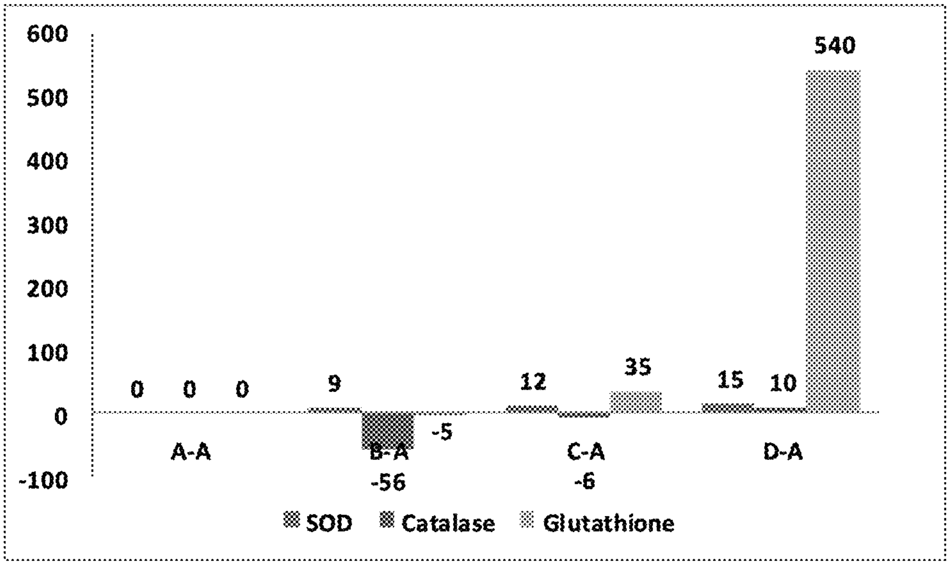
FIG. 30 depicts a graphical representation showing effect of chemotherapy on SOD activity in U/ml, catalase activity in micro mole/min/ml, and glutathione level in micro mole/ml of the patient described in case report 1 (Study group patient)

Further, SOD and catalase did not show significant activity, while glutathione activity increased considerably at one month after chemotherapy indicating reduction in ROS (Reactive Oxygen Species) generation (FIG. 30).

Figure 31:
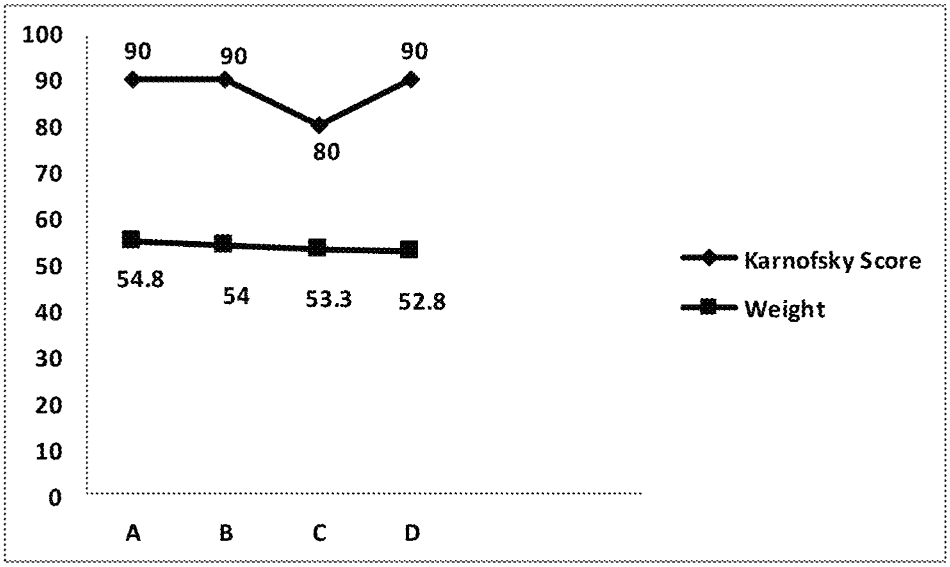
FIG. 31 depicts a graphical representation showing effect of chemotherapy on Karnofsky score and weight of the patient described in case report 1 (Study group patient)
Figure 32:
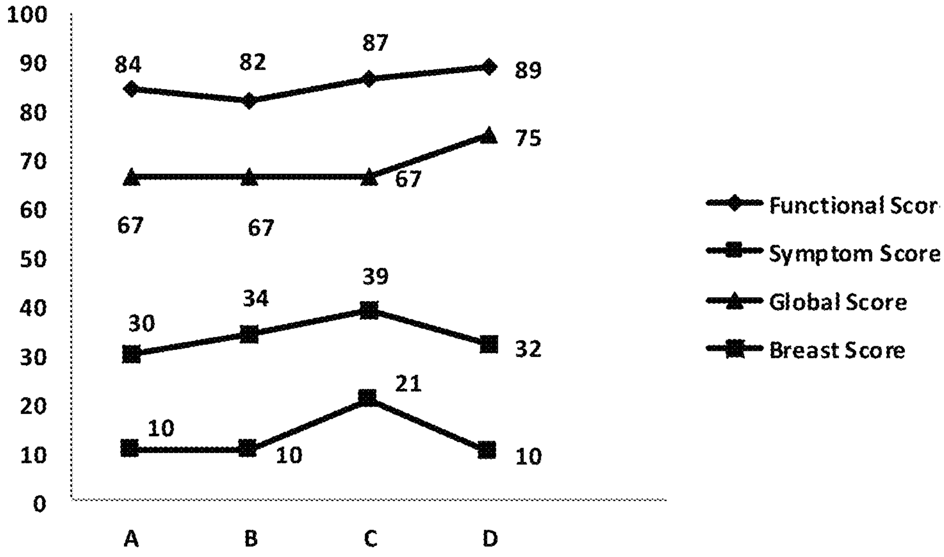
FIG. 32 depicts a graphical representation showing effect of chemotherapy on functional score, symptom score, global score, and breast score of the patient described in case report 1 (Study group patient)

4. Wellbeing of Patient Recorded as Karnofsky Score, QoL Scores (Functional, Symptoms, Global Scores and Breast Score) and Weight FIG. 31 and FIG. 32 indicate the scores at time points A to D.

Karnofsky and Functional scores show continuous increase from time point A to D indicating improvement in quality of life. Weight and global score remain stable throughout the period of observation while symptom score and breast score show stability from time point A to D with increase at time point C.

Overall quality of life and well-being appear to have improved which could be because of adjuvant treatment with oral pharmaceutical kit of the present disclosure.

Case Report 2:

Patient Information:

Age at diagnosis: 59 yrs.

Diagnosis: Ca Breast Right

Status at enrollment: Post-Operative

Date of diagnosis: 26 Nov. 2015

Histopathology report: Invasive duct carcinoma, grade III with high grade DCIS

Stage: pT2N1Mx Stage III

Grade: III

IHC: ER, PR, Her2 neu receptor—Negative (Triple Negative Breast Cancer)

Past medical/surgical history: Hysterectomy-2009/Tympanoplasty-1998, K/C/O-DM/HTN on conventional treatment, Cervical Spondylosis Family H/O-Mother: Ca Oesophagus, Father-Ca Stomach Treatment Details—

Surgery: Right Modified Radical Mastectomy—Left breast lumpectomy with vulval lumpectomy on 4 Dec. 2015 at a hospital in Pune.

Chemotherapy Details: 4 cycles of Inj. Doxorubicine 80 mg and Inj. Cyclophosphamide 840 mg taken from 25 Dec. 2015 to 26 Feb. 2016 and 4 cycles of Inj. Docetaxel 120 mg taken from 18 Mar. 2016 to 20 May 2016.

Results:

1. Chemotherapy Side Effects

Figure 33:
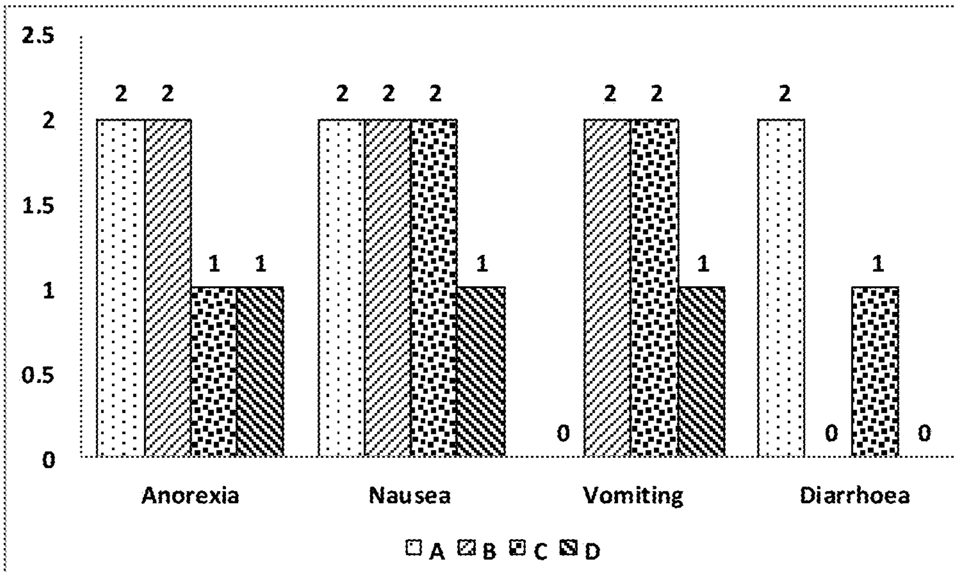
FIG. 33 depicts a graphical representation showing effect of chemotherapy on anorexia, nausea, vomiting and diarrhoea of the patient described in case report 2 (Control group patient)
Figure 34:
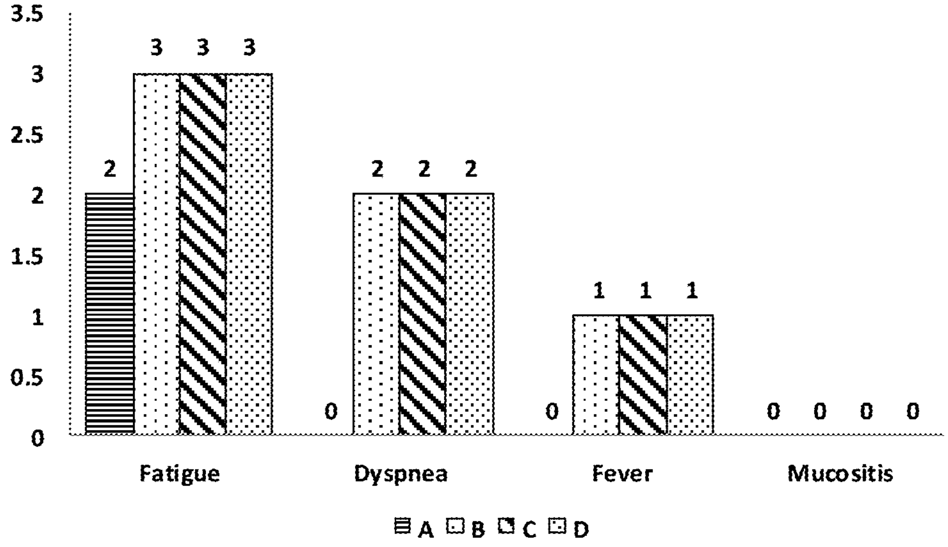
FIG. 34 depicts a graphical representation showing effect of chemotherapy on fatigue, dyspnea, fever, and mucositis of the patient described in case report 2 (Control group patient)
Figure 35:
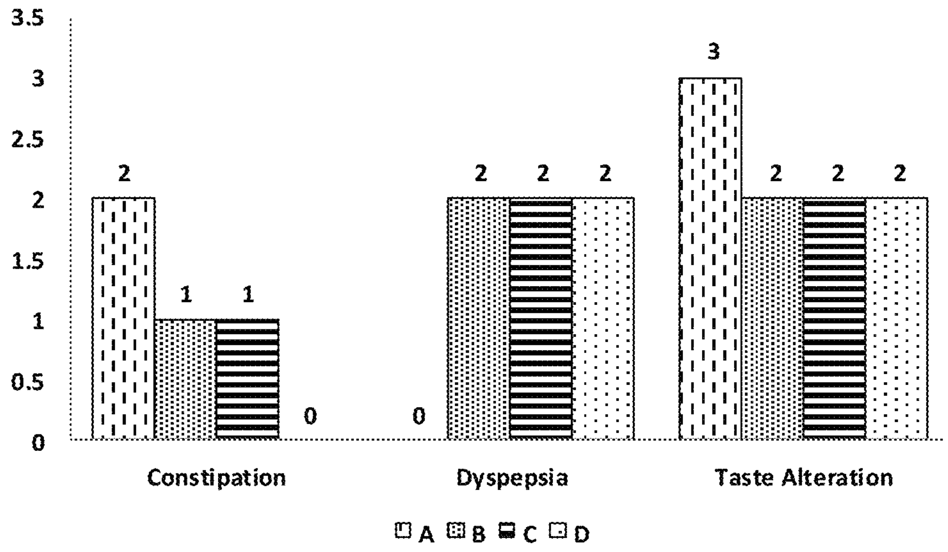
FIG. 35 depicts a graphical representation showing effect of chemotherapy on constipation, dyspepsia, and taste alteration of the patient described in case report 2 (Control group patient)

Out of commonly observed adverse effects, 11 significant symptoms were recorded in this study on the scale of 1-5 with grade ‘0’ denoting absence of symptom (except for taste alteration where the grading is 1-2, for dyspepsia the grading is 1-3 and for fatigue is 1-4) (FIGS. 33, 34 and 35). Since adverse effects of chemotherapy are detectable after 1 cycle of chemotherapy, time point A was recorded as values after 1 cycle of chemotherapy and all further points (from B to D) are compared with this time point A.

It can be seen from FIG. 33, anorexia is high at time points A and B, and nausea is high at time points A, B and C. At time point A, the patient has no symptom of vomiting which has risen to grade 2 at time points B and C. Diarrhoea is high at time point A, then reduced to 0 at time point B, appeared again at time point C to grade 1 and then subsided.

FIG. 34 and FIG. 35 show no change in symptoms such as dyspnea, dyspepsia and fever at time points B, C and D although much higher as compared to time point A. Fatigue from grade 2 at time point A has increased to grade 3 at time points B, C and D. Mucositis did not appear at any time point (FIG. 34). Constipation and taste alteration show initially higher level at time point A which decreases to grade 2 and 1, respectively at time points B, C, and D (FIG. 35).

2. Haematological and Biochemical Analysis—

TABLE 7

Data on haematological and biochemical investigations

| Time point | Hb *(12-16 g/dl) | WBC *(4000-11000/ cmm) | Platelet *(150000-450000/ cmm) | S. Bil *(0-1.2 mg/dl) | SGOT *(0-31 U/L) | SGPT *(0-32 U/L) | S Alkaline Phosphates *(44-147 U/L) | S Creatinine *(0.7-1.7 mg/dl) | CA 15.3 *(0-32 U/ml) | CRP *(0-6 mg/L) |
|---|---|---|---|---|---|---|---|---|---|---|
| A | 12.7 | 8500 | 249000 | 0.69 | 34.74 | 26.04 | 77.41 | 0.7 | 13.64 | 1.07 |
| B | 11.3 | 5100 | 363000 | ND | ND | ND | ND | 0.88 | ND | 5.13 |

TABLE 7-continued

Data on haematological and biochemical investigations

| Time point | Hb *(12-16 g/dl) | WBC *(4000-11000/ cmm) | Platelet *(150000-450000/ cmm) | S. Bil *(0-1.2 mg/dl) | SGOT *(0-31 U/L) | SGPT *(0-32 U/L) | S Alkaline Phosphates *(44-147 U/L) | S Creatinine *(0.7-1.7 mg/dl) | CA 15.3 *(0-32 U/ml) | CRP *(0-6 mg/L) |
|---|---|---|---|---|---|---|---|---|---|---|
| C | 10.4 | 14100 | 300000 | 0.6 | 22.12 | 16.93 | 158 | 0.75 | ND | 165.5 |
| D | 11.1 | 4000 | 227000 | 0.67 | 21.4 | 10.54 | 139 | 0.8 | 6.32 | 1.62 |

ND—Not done
*Denotes normal range of respective parameter.

From Table 7, it is evident that the state of hemoglobin appears to decrease during chemotherapy. While the values of WBC and platelets are within normal range except for time point C for WBC, when the patient was admitted in ICU. Similar increase is noted in CRP and alkaline phosphatase levels.

Figure 36:
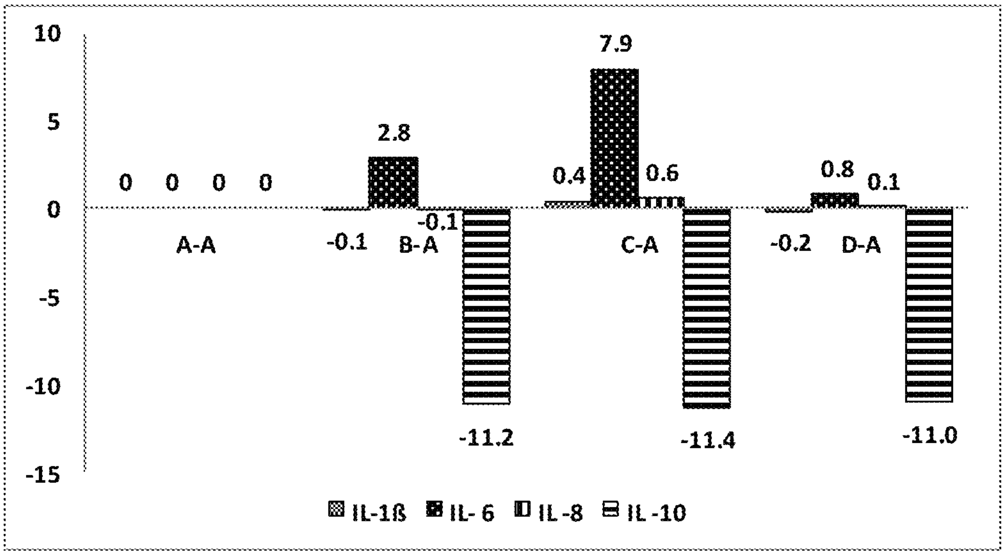
FIG. 36 depicts a graphical representation showing effect of chemotherapy on IL-1β, IL-6, IL-8, and IL-10 levels in pg/ml units of the patient described in case report 2 (Control group patient)

3. Immune and Oxidative Stress Status:

The activity of IL-1β and IL-8 in terms of fold change remains stable throughout the period of observation while levels of IL-10 are in negative range of fold change. Cytokine IL-6 increases at the end of chemotherapy while in 1 month this pro-inflammatory cytokine reduces considerably (FIG. 36).

Figure 37:
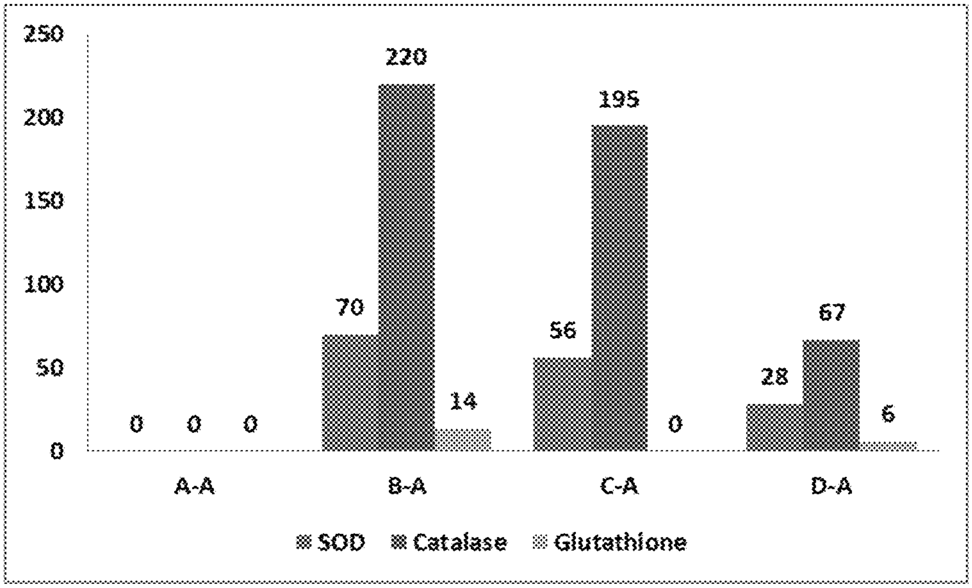
FIG. 37 depicts a graphical representation showing effect of chemotherapy on SOD activity in U/ml, catalase activity in micro mole/min/ml, and glutathione levels in micro mole/ml of the patient described in case report 2 (Control group patient)

The increase in catalase activity during chemotherapy indicates scavenging of $H_2O_2$ however it does not reflect in antioxidant status of the patient (FIG. 37).

Figure 38:
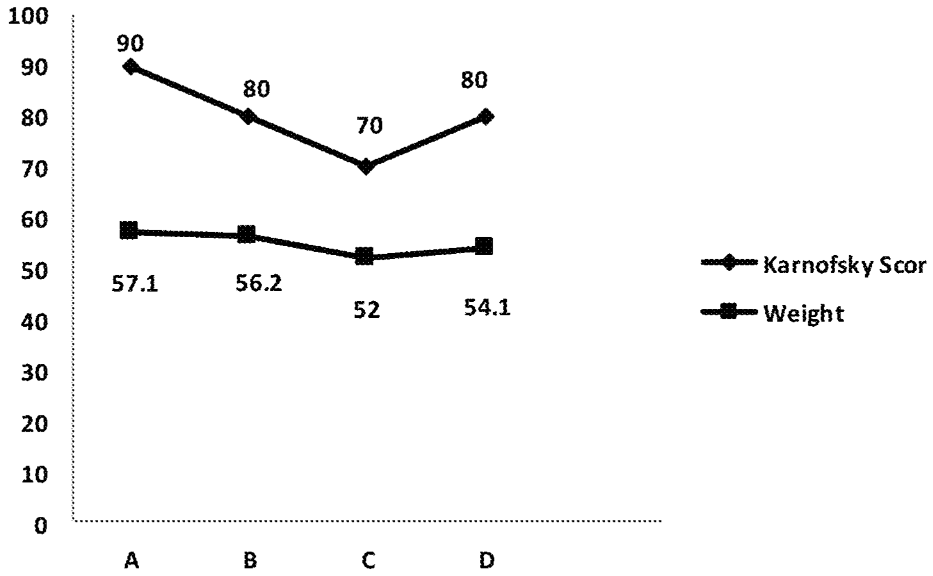
FIG. 38 depicts a graphical representation showing effect of chemotherapy on Karnofsky score and weight of the patient described in case report 2 (Control group patient)

4. Wellbeing of Patients Recorded as Karnofsky Score, QoL Scores (Functional, Symptoms, Global Scores and Breast Score) and Weight Karnofsky score reduces at the time points B and C which stabilizes at 1 month after chemotherapy. However the level has not reached up to the score of that of time point A. The weight remains almost constant throughout the period of observation (FIG. 38).

Figure 39:
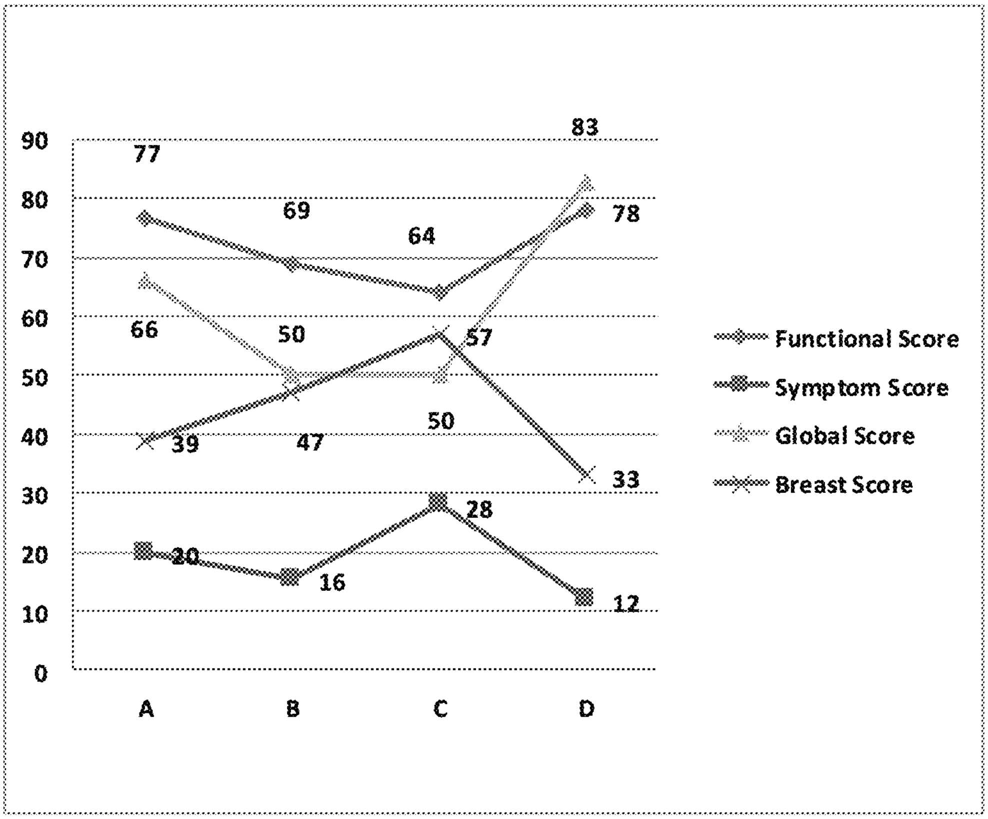
FIG. 39 depicts a graphical representation showing effect of chemotherapy on functional score, symptom score, global score, and breast score of the patient described in case report 2 (Control group patient)

Functional score and global score decrease progressively up to time point C but increase to their original level or above at time point D, while symptom score and breast scores show similar upward trend till time point C, which decrease at 1 month after chemotherapy (FIG. 39).

On comparison of two case reports, it was observed that taste alteration, nausea and vomiting symptoms were higher in Case 2 at all the time points which were absent in Case 1 at those time points. Similarly, fever and constipation in Case 2 were higher throughout the observation period as against observed in Case 1, only at time point D. Dyspnea and dyspepsia were observed in Case 2 at all the time points, whereas in Case 1 these symptoms were present only on time point A and B respectively, and at lower gradation. These symptoms then disappeared till the observation period. Similarly diarrhoea and mucositis did not appear in Case 1 at all the time points whereas in Case 2 diarrhoea which was present earlier subsided slowly and mucositis did not appeared at all. It is important to note that the myelosuppression in Case 2 was so severe that patient had to be admitted to ICU at time point C. Quality of life as shown by Karnofsky and Functional score progressively improved in Case 1 as against Case 2. These results show that intervention of the pharmaceutical kit of the present disclosure is favorable to the patient during the course of chemotherapy.

Overall, it is evident from the examples 2 and 3 including bulk case control study and case reports that the pharmaceutical kit of the present disclosure alleviates the symptoms of chemotherapy such as nausea, vomiting, anorexia, fever, taste alteration, fatigue and mucositis in breast cancer patients leading to better quality of life. It is further evident based on Karnofsky score, Functional score, Symptom score, and Global score that the quality of life of the patients improved significantly with the use of the pharmaceutical kit of the present disclosure. Also improvement in immune and oxidative status added to the betterment of the quality of life of the breast cancer patients.

This may have long term positive effects on the disease status and quality of life of these patients treated with chemotherapy. Use of the pharmaceutical kit of the present disclosure may prove to be beneficial in other cancers and diseases for which chemotherapy is a treatment of choice.

Example 4

Efficacy Studies of the Pharmaceutical Kit of the Present Disclosure Compared to a Composition without SBD During Chemotherapy in Breast Cancer Patients This example assesses and compares usefulness of the present pharmaceutical kit of the present disclosure vis'-a-vis' another composition containing MKD, Ananta Vati, Praval Pishti and PDG for alleviating adverse effects of chemotherapy in breast cancer patients. The present pharmaceutical kit contains SBD, MKD, PDG, and Ananta Vati while other composition of MKD, Ananta Vati, Praval Pishti, and PDG does not contain SBD. SBD in the pharmaceutical kit of the present disclosure has an additive property of immunomodulation and rejuvenation. Thus, the 4 components of pharmaceutical kit of the present disclosure including MKD, Ananta Vati, PDG, and SBD have synergistic effect in reducing the toxic side effects of chemotherapy and improving quality of life as compared to the composition without SBD mentioned above. To study this synergism, three groups of breast cancer patients receiving (GR1) the pharmaceutical kit of the present disclosure, (GR2) composition of MKD, Ananta vati, Praval Pishti and PDG without SBD and (GR3) control patients receiving only chemotherapy were compared for chemotherapy induced side effects and quality of life.

In this study, 49 breast cancer patients, treated with surgery, scheduled for chemotherapy were enrolled. Out of these, 16 patients were given pharmaceutical kit of present disclosure along with chemotherapy (Group GR1), 18 patients received composition of MKD, Ananta vati, Praval Pishti and PDG along with chemotherapy (Group GR2) and remaining 15 patients received only chemotherapy (Group GR3—Control group). The stage and grade of the disease were matched for all the three groups. Treatment for GR1 and GR2 was given at start of chemotherapy and continued till completion of chemotherapy.

Inclusion Criteria for Enrolling Patients in this Study

Female patients: Age group between 25-75 years, operated for breast cancer, who were in Stage I, II and III of the disease and were eligible for chemotherapy.

Exclusion Criteria for Enrolling Patients in this Study

Patients who were on other Ayurvedic drugs for cancer or any other ailment and patients with distant metastasis and recurrence.

Outcome Measures—Time Points for Assessment of Outcome Measures—

A—Before chemotherapy for quality of life while

A—1 week after 1st cycle of chemotherapy for symptoms of adverse effects

B—End of chemotherapy

A. Clinical Investigations

The Patients were Followed for:

Assessment of adverse effects clinically and graded using CTCAE 4.03 Version (Grading of symptoms on scale of 1-5 with grade '0' denoting absence of symptom (except for taste alteration where the grading is 1-2, for dyspepsia the grading is 1-3 and for fatigue is 1-4). Lower scale denotes less severity of the symptoms.

Assessment of performance status using Karnofsky score (Grading for well-being on 0 to 100 scale, higher score denotes better performance).

Assessment of Quality of Life (QoL) using Questionnaire QLQ C30 (designed for all types of cancers) and BR 23 (specially designed for breast cancer status) of EORTC determined on the basis of patients' own perspective about her well-being.

QLQ C30 can be interpreted as—

1. Symptomatology (Symptom score)
2. Ability to perform routine activities (Functional score)
3. Overall well-being (Global score)

Karnofsky score and scoring for QoL are internationally accepted means of scoring symptoms and quality of life for cancer patients used in various studies in clinical trials.

The data was analyzed as fold change in a given parameter compared to its level at time point A. For symptoms and scores paired T test was applied.

Experiment 1: Alleviation of Adverse Effects of Chemotherapy in Breast Cancer Patients Using Pharmaceutical Kit of the Present Disclosure and Composition of MKD, Ananta Vati, Praval Pishti and PDG as Well as Absolute Control Out of commonly observed adverse effects, 7 significant symptoms were recorded in this study on the scale of 1-5 with grade '0' denoting absence of symptom (except for taste alteration where the grading is 1-2, for dyspepsia the grading is 1-3 and for fatigue is 1-4).

The mean of gradation at both the time points was recorded for all the three groups. The observations for each group at time point B were compared with respective time point A (After 1 cycle of chemotherapy, since chemotherapy induced adverse effects show up after chemotherapy starts) and fold change histograms were plotted. Comparison of average values of each symptom and score at time point B among the three groups was also performed and described in the text.

Figure 40:
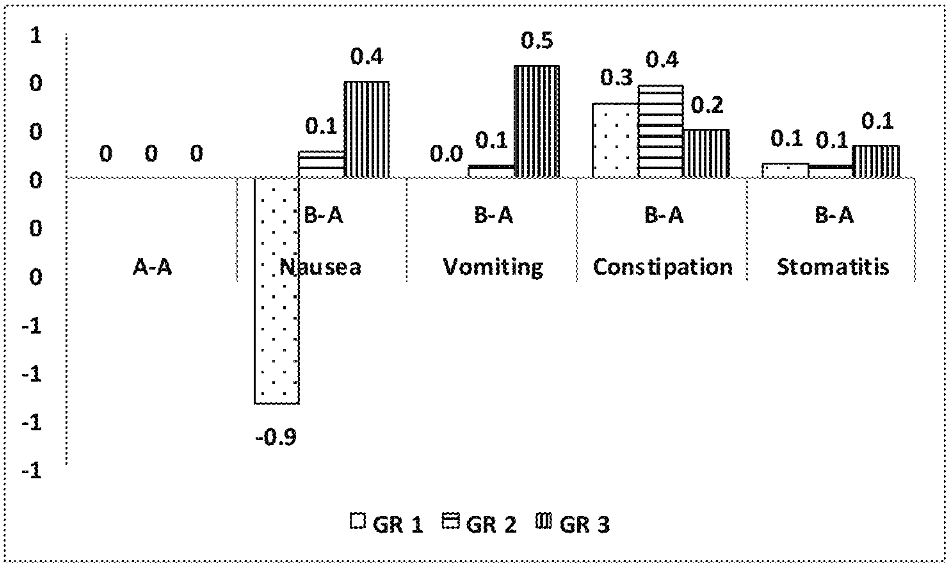
FIG. 40 depicts a graphical representation showing comparison of reduction in adverse effects such as nausea, vomiting, constipation and stomatitis in group treated with present pharmaceutical kit (GR1), treated with combination of MKD, Ananta vati, Praval Pishti and PDG (GR2) and control group (GR3)

Results:

Nausea—GR3 shows significant increase in nausea during the period of chemotherapy (time points—A to B). GR2 indicates significant (p=0.056) decrease and GR1 reveals negative fold decrease in nausea compared to its time point A. GR1 shows very highly significant (p=0.0005) and highly significant (p=0.0015) reduction compared to GR3 and GR2, respectively (FIG. 40).

Vomiting—GR3 shows significant increase in vomiting during the period of chemotherapy (time points—A to B). GR1 and GR2 show significant decrease in this symptom with p values of (p=0.06) and (p=0.005) at time point B as compared to GR3, respectively. It can be seen from FIG. 40 that GR1 shows clear trend of decrease in vomiting as compared to GR2.

Constipation—All the three groups show increase in constipation at time point B as compared to their respective time point A. However, GR1 indicates less increase as compared to GR2 at time point B (FIG. 40).

Stomatitis—All the three groups show increase in stomatitis at time point B as compared to their respective time point A. However, GR1 and GR2 indicate less increase as compared to GR3 at time point B (FIG. 40).

Figure 41:
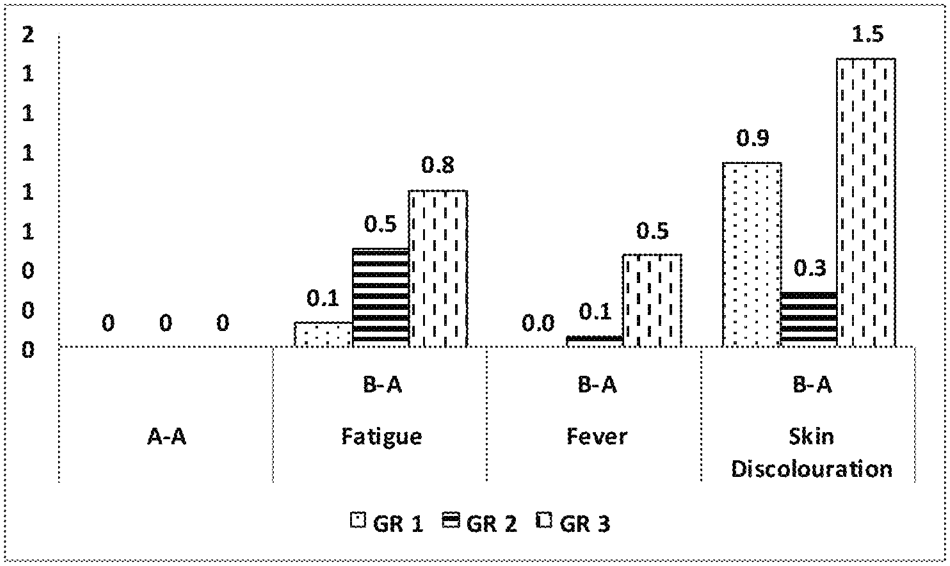
FIG. 41 depicts a graphical representation showing comparison of reduction in adverse effects such as fatigue, fever and skin discoloration in group treated with present pharmaceutical kit (GR1), treated with combination of MKD, Ananta vati, Praval Pishti and PDG (GR2) and control group (GR3)

Fatigue—All the three groups show increase in fatigue at time point B as compared to their respective time point A. GR1 and GR2 indicate less increase as compared to GR3 at time point B. However, GR1 shows much less fatigue as compared to GR2 and significant decrease (p=0.048) as compared to GR3 (FIG. 41).

Fever—GR3 shows significant increase in fever during the period of chemotherapy (time points—A to B). GR1 and GR2 show significant decrease in this symptom with p values of (p=0.0067) and (p=0.0049) at time point B as compared to GR3, respectively. It can be seen from FIG. 41 that GR1 shows clear trend of decrease in fever as compared to GR2.

Skin discoloration—All the three groups show increased skin discoloration score upon chemotherapy at time point B as compared to their respective time point A. Moreover, GR1 and GR2 show significant difference (p=0.091) and very highly significant difference (p=0.00001), respectively when compared to GR3. Within GR1 and GR2, GR2 shows highly significant (p=0.007) decrease in skin discoloration score as compared to GR1 (FIG. 41).

Experiment 2: Assessment of Quality of Life in Breast Cancer Patients Using Pharmaceutical Kit of the Present Disclosure and Composition of MKD, Ananta Vati, Praval Pishti and PDG as Well as Absolute Control Karnofsky score, weight, Functional score, Symptom score, and Global score were recorded. To represent this score in graphs the mean values at each time point were recorded for all the three groups.

Result:

Karnofsky score—GR1 shows increased Karnofsky score at time point B compared to time point A whereas GR2 and GR3 both indicate considerable decreased score at time point B compared to their respective time point A. GR1 revealed significantly higher (p=0.042 and p=0.03) Karnofsky score compared to GR2 and GR3, respectively (FIG. 42A).

Weight—All the three groups show decreased weight at time point B compared to their respective time point A (FIG. 42A).

Functional score—GR1 shows increased Functional score at time point B compared to time point A whereas GR2 and GR3 both indicate considerable decreased score at time point B compared to their respective time point A. GR1 revealed very highly significant (p=0.00058) and significant (p=0.024) higher Functional score compared to GR2 and GR3, respectively (FIG. 42B).

Symptom score—All the three groups show increased symptom score at time point B compared to their respective time point A. However, GR1 shows minimum increase as compared to GR2 and GR3, while GR2 shows less increase as compared to GR3 (FIG. 42B).

Global score—GR1 and GR3 show increased Global score while GR2 shows decrease Global score at time point B compared to their respective time point A. GR1 indicates better global score than GR3 at time point B (FIG. 42B).

The example 4 was to assess performance of pharmaceutical kit of present disclosure with that of composition consisting MKD, Ananta vati, Praval Pishti and PDG and absolute control. Overall, it is evident that the pharmaceutical kit of the present disclosure and composition consisting MKD, Ananta vati, Praval Pishti and PDG show better outcome with respect to alleviation of adverse symptoms due to chemotherapy as well as improved quality of life in breast cancer patients as compared to absolute control. It is further evident that the pharmaceutical kit of present disclosure proved to be more beneficial in case of adverse symptoms such as nausea, vomiting, fatigue and fever; and parameters of quality of life such as Karnofsky score, Functional score, Symptom score and Global score as compared to the composition consisting of MKD, Ananta vati, Praval Pishti and PDG.

It is quite evident that the components of the pharmaceutical kit of the present disclosure have synergistic effect on the control of disease and improved quality of life of the patients treated with chemotherapy in cancer and may prove to be beneficial in several other diseases treated with chemotherapy.

TECHNICAL ADVANCEMENTS

The present disclosure described herein above has several technical advantages including, but not limited to, the realization of a pharmaceutical kit:

- that produces enhanced anti-inflammatory, anti-oxidant and immunomodulatory effect;
- that alleviates the adverse effects of chemotherapy such as nausea, vomiting, anorexia, fever, taste alteration, fatigue and mucositis; and
- that improves quality of life and functional ability of the patients treated with chemotherapy.

The embodiments as described herein above, and various features and advantageous details thereof are explained with reference to the non-limiting embodiments in the description. Descriptions of well-known aspects, components, and molecular biology techniques are omitted so as to not unnecessarily obscure the embodiments herein.

The foregoing description of specific embodiments so fully reveal the general nature of the embodiments herein, that others can, by applying current knowledge, readily modify and/or adapt for various applications of such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein. Further, it is to be distinctly understood that the foregoing descriptive matter is to be interpreted merely as illustrative of the disclosure and not as a limitation.

Having described and illustrated the principles of the present disclosure with reference to the described embodiments, it will be recognized that the described embodiments can be modified in arrangement and detail without departing from the scope of such principles.

While considerable emphasis has been placed herein on the particular features of this disclosure, it will be appreciated that various modifications can be made, and that many changes can be made in the preferred embodiment without departing from the principles of the disclosure. These and other modifications in the nature of the disclosure or the preferred embodiments will be apparent to those skilled in the art from the disclosure herein, whereby it is to be distinctly understood that the foregoing descriptive matter is to be interpreted merely as illustrative of the disclosure and not as a limitation.

The invention claimed is:

1. A pharmaceutical kit for alleviating adverse effects of chemotherapy comprising:

- a first container containing Suvarna Bhasmadi Vati (SBD) in an amount in the range of 800 mg/day to 1000 mg/day;
- a second container containing Mouktikyukta Kamdudha Vati (MKD) in an amount in the range of 800 mg/day to 1200 mg/day;
- a third container containing Padmakadi Ghrut (PDG) in a thick, viscous form in an amount in the range of 8 gm/day to 12 gm/day; and
- a fourth container containing Ananta Vati in an amount in the range of 1.8 mg/day to 2.2 gm/day,
- wherein said SBD comprises:
  - Suvarna bhasma in an amount ranging from 2 wt % to 7 wt % of the total weight of the SBD;
  - Mouktik bhasma in an amount ranging from 20 wt % to 35 wt % of the total weight of the SBD;
  - Guduchi sattva in an amount ranging from 45 wt % to 60 wt % of the total weight of the SBD; and
  - at least one excipient in an amount ranging from 5 wt % to 30 wt % of the total weight of the SBD,
- wherein said Suvarna bhasma contains gold (Au) in an amount not less than 85% w/w.

2. The pharmaceutical kit as claimed in claim 1, wherein said MKD comprises:

- Mouktik bhasma in an amount ranging from 10 wt % to 14 wt % of the total weight of the MKD;
- Shankha bhasma in an amount ranging from 10 wt % to 14 wt % of the total weight of the MKD;
- Shouktik bhasma in an amount ranging from 10 wt % to 14 wt % of the total weight of the MKD;
- Kapardik bhasma in an amount ranging from 10 wt % to 14 wt % of the total weight of the MKD;
- Praval bhasma in an amount ranging from 10 wt % to 14 wt % of the total weight of the MKD;
- Guduchi sattva in an amount ranging from 10 wt % to 14 wt % of the total weight of the MKD;
- Shudhha Gairik in an amount ranging from 10 wt % to 14 wt % of the total weight of the MKD; and
- at least one excipient in an amount ranging from 10 wt % to 25 wt % of the total weight of the MKD.

3. The pharmaceutical kit as claimed in claim 1, wherein said PDG comprises:

- an extract of petals and stalks of Padmak, wherein said extract of Padmak is obtained by using at least one solvent selected from the group consisting of alcohol, water and mixture thereof;
- an extract of whole Durva plant, wherein said extract of whole Durva plant is obtained using at least one solvent selected from the group consisting of alcohol, water and mixture thereof;

a decoction of roots of Ananta, wherein said decoction of roots of Ananta is obtained using at least one solvent selected from the group consisting of alcohol, water and mixture thereof; and Ghee obtained from cow's milk in an amount ranging from 95 wt % to 98 wt % of the total weight of the PDG.

4. The pharmaceutical kit as claimed in claim 3, wherein the amount of the combined extract of petals and stalks of Padmak, whole Durva plant, and roots of Ananta is in the range of 2 wt % to 10 wt % of the total weight of PDG, and wherein the weight ratio of the extract of petals and stalks of Padmak to the extract of whole Durva plant to the decoction of roots of Ananta is 1:1:1.

5. The pharmaceutical kit as claimed in claim 1, wherein said Ananta vati comprises:

powder obtained from dried roots of Ananta in an amount ranging from 75 wt % to 92 wt % of the total weight of the Ananta vati, wherein the powder has a particle size in the range of 150 to 180 microns; and at least one excipient in an amount ranging from 8 wt % to 25 wt % of the total weight of the Ananta vati.

6. The pharmaceutical kit as claimed in claim 1, wherein said excipient is a binder.

7. The pharmaceutical kit as claimed in claim 2, wherein said excipient is a binder.

8. The pharmaceutical kit as claimed in claim 5, wherein said excipient is a binder.

9. The pharmaceutical kit as claimed in claim 6, wherein said binder is selected from the group consisting of gum acacia, guar gum, and xanthan gum.

10. The pharmaceutical kit as claimed in claim 7, wherein said binder is selected from the group consisting of gum acacia, guar gum, and xanthan gum.

11. The pharmaceutical kit as claimed in claim 8, wherein said binder is selected from the group consisting of gum acacia, guar gum, and xanthan gum.

12. A method of alleviating adverse effects of chemotherapy by using a pharmaceutical kit as claimed in claim 1, wherein said kit is administered as follows:

Suvarna Bhasmadi Vati (SBD) in an amount in the range of 800 mg/day to 1000 mg/day and is administered 2 tablets twice a day;

Mouktikyukta Kamdudha Vati (MKD) in an amount in the range of 800 mg/day to 1200 mg/day and is administered as 2 tablets twice a day;

Padmakadi Ghrut (PDG) in a thick, viscous form in an amount in the range of 8 gm/day to 12 gm/day and is administered in an amount as 1 tsp twice a day; and Ananta Vati in an amount in the range of 1.8 mg/day to 2.2 gm/day and is administered in an amount as 4 tablets twice a day.

* * * * *